United States Patent
Hobbs et al.

(10) Patent No.: US 6,936,167 B2
(45) Date of Patent: Aug. 30, 2005

(54) SYSTEM AND METHOD FOR PERFORMING MULTIPLE PARALLEL CHROMATOGRAPHIC SEPARATIONS

(75) Inventors: Steven E. Hobbs, West Hills, CA (US); Hau H. Duong, Pasadena, CA (US); Scott G. Beach, Manhattan Beach, CA (US)

(73) Assignee: Nanostream, Inc., Pasadena, CA (US)

( * ) Notice: Subject to any disclaimer, the term of this patent is extended or adjusted under 35 U.S.C. 154(b) by 71 days.

(21) Appl. No.: 10/696,354

(22) Filed: Oct. 28, 2003

(65) Prior Publication Data

US 2004/0089607 A1 May 13, 2004

Related U.S. Application Data

(60) Provisional application No. 60/506,452, filed on Sep. 26, 2003, and provisional application No. 60/422,901, filed on Oct. 31, 2002.

(51) Int. Cl.$^7$ .............................................. B01D 15/08
(52) U.S. Cl. .................... 210/198.2; 210/656; 210/143; 422/70; 422/100
(58) Field of Search .................................. 210/635, 656, 210/198.2, 502.1, 659, 143; 422/70, 100

(56) References Cited

U.S. PATENT DOCUMENTS

| | | | |
|---|---|---|---|
| 5,070,606 A | 12/1991 | Hoopman et al. | 29/890.03 |
| 5,376,252 A | 12/1994 | Ekström et al. | 204/299 R |
| 5,571,410 A | 11/1996 | Swedberg et al. | 210/198.2 |
| 5,658,413 A | 8/1997 | Kaltenbach et al. | 156/272.8 |
| 5,690,763 A | 11/1997 | Ashmead et al. | 156/60 |
| 5,744,366 A | 4/1998 | Kricka et al. | 436/63 |
| 5,792,943 A | 8/1998 | Craig | 73/61.52 |
| 5,804,701 A | 9/1998 | Berger | 73/23.42 |
| 5,846,396 A | 12/1998 | Zanzucchi et al. | 204/601 |
| 5,872,010 A | 2/1999 | Karger et al. | 436/173 |

(Continued)

FOREIGN PATENT DOCUMENTS

| | | |
|---|---|---|
| EP | 1 106 244 A2 | 6/2001 |
| WO | WO 95/02178 | 1/1995 |
| WO | WO 98/07069 | 2/1998 |
| WO | WO 98/45693 | 10/1998 |
| WO | WO 99/19717 | 4/1999 |
| WO | WO 00/21659 | 4/2000 |
| WO | WO 00/31528 | 6/2000 |
| WO | WO 00/72970 A1 | 12/2000 |
| WO | WO 01/09598 A1 | 2/2001 |
| WO | WO 01/14064 A1 | 3/2001 |
| WO | WO 01/30490 A1 | 5/2001 |
| WO | WO 01/38865 A1 | 5/2001 |
| WO | WO 01/86283 A2 | 11/2001 |
| WO | WO 02/10732 A1 | 2/2002 |

(Continued)

OTHER PUBLICATIONS

Ericson, Christer et al., *Electroosmosis– and Pressure–Driven Chromatography in Chips Using Continuous Beds*, "Analytical Chemistry," vol. 72, No. 1, Jan. 1, 2000, pp. 81–87.

(Continued)

*Primary Examiner*—Ernest G. Therkorn
(74) *Attorney, Agent, or Firm*—Vincent K. Gustafson

(57) ABSTRACT

Systems and methods for performing multiple parallel chromatographic separations are provided. Microfluidic cartridges containing multiple separation columns allow multiple separations to be performed in a limited space by a single instrument containing high-pressure pumps and analyte detectors. The use of pressure fit interfaces allows the microfluidic cartridges to easily be removed and replaced within the instrument, either manually or robotically.

18 Claims, 22 Drawing Sheets

U.S. PATENT DOCUMENTS

| | | | |
|---|---|---|---|
| 5,882,571 A | 3/1999 | Kaltenbach et al. | 264/400 |
| 5,917,184 A | 6/1999 | Carson et al. | 250/288 |
| 6,048,498 A | 4/2000 | Kennedy | 422/99 |
| 6,066,848 A | 5/2000 | Kassel et al. | 250/288 |
| 6,073,482 A | 6/2000 | Moles | 73/53.01 |
| 6,074,725 A | 6/2000 | Kennedy | 428/188 |
| 6,090,278 A | 7/2000 | Lally et al. | 210/198.2 |
| 6,129,973 A | 10/2000 | Martin et al. | 428/166 |
| 6,136,414 A | 10/2000 | Aizawa et al. | 428/156 |
| 6,167,910 B1 | 1/2001 | Chow | 137/827 |
| 6,171,486 B1 | 1/2001 | Green et al. | 210/198.2 |
| 6,191,418 B1 | 2/2001 | Hindsgaul et al. | 250/288 |
| 6,221,252 B1 | 4/2001 | Hargro et al. | 210/656 |
| 6,235,471 B1 | 5/2001 | Knapp et al. | 435/6 |
| 6,240,790 B1 | 6/2001 | Swedberg et al. | 73/863.21 |
| 6,264,892 B1 | 7/2001 | Kaltenbach et al. | 422/68.1 |
| 6,296,771 B1 | 10/2001 | Miroslav | 210/656 |
| 6,318,157 B1 | 11/2001 | Corso et al. | 73/61.52 |
| 6,404,493 B1 | 6/2002 | Altendorf | 356/337 |
| 6,410,915 B1 | 6/2002 | Bateman et al. | 250/288 |
| 6,430,512 B1 | 8/2002 | Gallagher | 702/22 |
| 6,437,345 B1 | 8/2002 | Bruno-Raimondi et al. | 250/458.1 |
| 6,461,515 B1 | 10/2002 | Safir et al. | 210/656 |
| 6,485,069 B1 | 11/2002 | Anderson | 292/175 |
| 6,491,816 B2 | 12/2002 | Petro | 210/198.2 |
| 6,494,614 B1 | 12/2002 | Bennett et al. | 366/336 |
| 6,499,499 B2 * | 12/2002 | Dantsker et al. | 137/1 |
| 6,532,978 B1 | 3/2003 | Müller-Kuhrt et al. | 137/1 |
| 6,533,840 B2 | 3/2003 | Martin et al. | 95/45 |
| 6,537,501 B1 | 3/2003 | Holl et al. | 422/101 |
| 6,537,506 B1 | 3/2003 | Schwalbe et al. | 422/130 |
| 6,547,941 B2 | 4/2003 | Kopf-Sill et al. | 204/452 |
| 6,581,441 B1 | 6/2003 | Paul | 73/61.52 |
| 6,613,581 B1 | 9/2003 | Wada et al. | 436/518 |
| 6,627,446 B1 | 9/2003 | Roach et al. | 436/43 |
| 6,743,356 B1 | 6/2004 | Fermier et al. | 210/198.2 |
| 6,749,814 B1 | 6/2004 | Bergh et al. | 422/130 |
| 2002/0003001 A1 | 1/2002 | Weigl et al. | 137/806 |
| 2002/0008032 A1 | 1/2002 | Hayenga | 204/603 |
| 2002/0036018 A1 | 3/2002 | McNeely et al. | 137/806 |
| 2002/0041827 A1 | 4/2002 | Yager et al. | 422/57 |
| 2002/0158022 A1 | 10/2002 | Huang et al. | 210/656 |
| 2002/0189947 A1 | 12/2002 | Paul et al. | 204/461 |
| 2002/0199094 A1 | 12/2002 | Strand et al. | 713/150 |
| 2003/0089663 A1 | 5/2003 | Petro et al. | 210/656 |
| 2003/0092056 A1 | 5/2003 | Nagasawa | 435/6 |
| 2003/0150555 A1 | 8/2003 | Gandhi et al. | 156/292 |
| 2003/0162304 A1 | 8/2003 | Dority et al. | 436/180 |
| 2003/0180711 A1 | 9/2003 | Turner et al. | 435/4 |
| 2004/0020834 A1 | 2/2004 | Mincsovics et al. | 210/198.2 |

FOREIGN PATENT DOCUMENTS

| | | |
|---|---|---|
| WO | WO 02/28509 A2 | 4/2002 |
| WO | WO 02/28532 A2 | 4/2002 |
| WO | WO 02/30486 A2 | 4/2002 |
| WO | WO 03/052428 A1 | 6/2003 |
| WO | WO 03/054524 A1 | 7/2003 |

OTHER PUBLICATIONS

Zhang, Bailin et al., *High–Throughput Microfabricated CE/ESI–MS: Automated Sampling from a Microwell Plate,* "Analytical Chemistry,"vol. 73, No. 11, Jun. 1, 2001, pp. 2675–2681.

Abian, J., *The Coupling of Gas and Liquid Chromatography with Mass Spectrometry,* "Journal of Mass Spectrometry," 34, 157–168, (1999).

Kameoka, Jun et al., *Polymeric Microfluidic Chip for CE/MS Determination of Small Molecules,* "Analytical Chemistry," vol. 73, No. 9, May 1, 2001, pp. 1935–1941.

Svedberg, Malin et al., "Electrospray from a Plastic Chip," *Micro Total Analysis Systems,* J.M. Ramsey and A. van den Berg (eds.), 2001, Kluwer Academic Publishers, the Netherlands, pp. 335–336.

"Multi–parallel HPLC," Web document published at: http://www.sepiatec.com/download/phplc.pdf, date unknown.

God, Ralf et al., "Using multiparallel HPLC for purification in drug discovery from nature," Application Note, 2003, International Scientific Communications, Inc.

Zhang, B. et al., *Microfabricated Devices for Capillary Electrophoresis–Electrospray Mass Spectrometry,* "Analytical Chemistry," vol. 71, No. 15, Aug. 1, 1999, pp. 3258–3264.

Moore, Roger E. et al., *A Microscale Electrospray Interface Incorporating a Monolithic, Poly(styrene–divinylbenzene) Support for On–Line Liquid Chromatography/Tandem Mass Spectrometry Analysis of Peptides and Proteins,* "Analytical Chemistry," vol. 70, No. 23, Dec. 1, 1998, pp. 4879–4884.

Little, David et al., "A Parallel LC–MS/MS System for High Throughput Quantification in Drug Discovery," Application Note 248, Waters/Micromass, May 2000.

Dunn, John A. et al., "A Parallel LC/MS/MS System for the High Throughput Quantification of Clinical Trial Samples. A Validation Study," Application Note, Waters/Micromass Oct. 2002.

Tan, Aimin et al, *Chip–Based Solid–Phase Extractrion Pretreatment for Direct Electrospray Mass Spectrometry Analysis Using an Array of Monolithic Columns in a Polymeric Substrate,* "Analytical Chemistry," vol. 75, No. 20, Oct. 15, 2003, pp. 5504–5511.

Lin, Yuehe et al., "Microfluidic Devices on Polymer Substrates for Bioanalytical Applications," Web document published at: www.pnl.gov/microcats/aboutus/publications/microchemical/Microtechpresentation.pdf, 1999.

Finot, Michael et al., "High Throughput Pharmaceutical Formulation Evaluation and Analysis Using Capillary Electrochromatography on a Microfluidic Chip," *Micro Total Analysis Systems,* J.M. Ramsey and A. van den Berg (eds.), 2001, Kluwer Academic Publishers, the Netherlands, pp. 480–482.

Jemere, Abebaw B. et al., "Microchip–Based Selective Preconcentration Using Protein A Immunoaffinity Chromatography," *Micro Total Analysis Systems,* J.M. Ramsey and A. van den Berg (eds.), 2001, Kluwer Academic Publishers, the Netherlands, pp. 501–502.

"HPLC: Micro LC/MS Analysis of Biological Samples," Web publication; http://www.sge.com, Apr. 1, 1998.

Chou, Hou–pu et al., "Disposable Microdevices for DNA Analysis and Cell Sorting," Proc. Solid–State Sensor and Actuator Workshop, SC, Jun. 8–11, 1998, pp. 11–14.

Delamarche, Emmanuel et al., *Microfluidic Networks for Chemical Patterning of Substrates: Design and Application to Bioassays,* "Journal of the American Chemical Society," 1998, 120, 500–508.

Harley, John C. et al., "System Design of Two Dimensional Microchip Separation Devices," *Micro Total Analysis Systems,* J.M. Ramsey and A. van den Berg (eds.), 2001, Kluwer Academic Publishers, the Netherlands, pp. 63–65.

Sato, Kiichi et al., "Integrated Immunoassay System Using Multichannel Microchip for Simultaneous Determination," *Micro Total Analysis Systems*, J.M. Ramsey and A. van den Berg (eds.), 2001, Kluwer Academic Publishers, the Netherlands, pp. 511–512.

Voldman, Joel et al., *An Integrated Liquid Mixer/Valve*, "Journal of Microelectromechanical Systems," vol. 9, No. 3, Sep. 2000.

Duffy, David C. et al, *Rapid Prototyping of Microfluidic Systems in Poly(dimethylsiloxane)*, "Analytical Chemistry," vol. 70, No. 23, Dec. 1, 1998, pp. 4974–4984.

Seiler, Kurt et al., *Planar Glass Chips for Capillary Electrophoresis: Repetitive Sample Injection, Quantitation, and Separation Efficiency*, "Analytical Chemistry," 1993, 65, 1481–1488.

MacNair, John E. et al., *Ultrahigh–Pressure Reversed–Phase Capillary Liquid Chromatography: Isocratic and Gradient Elution Using Columns Packed with 1.0–μm Particles*, "Analytical Chemistry," vol. 71, No. 3, Feb. 1, 1999, pp. 700–708.

\* cited by examiner

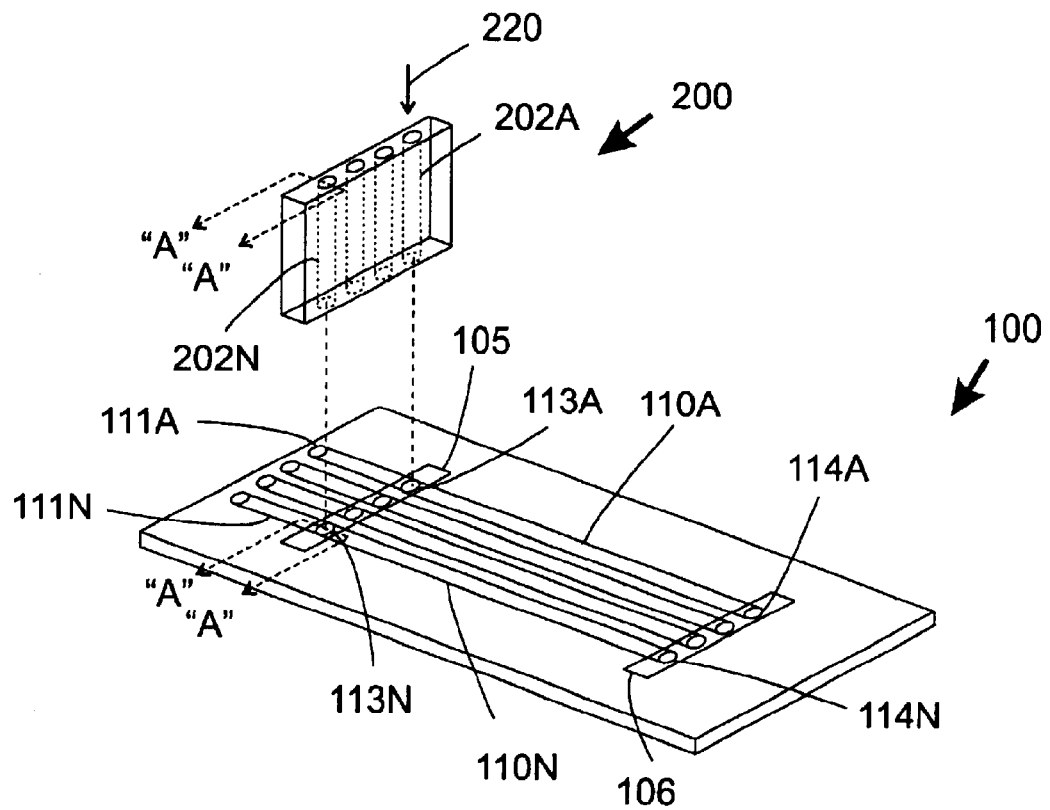
FIG._1A
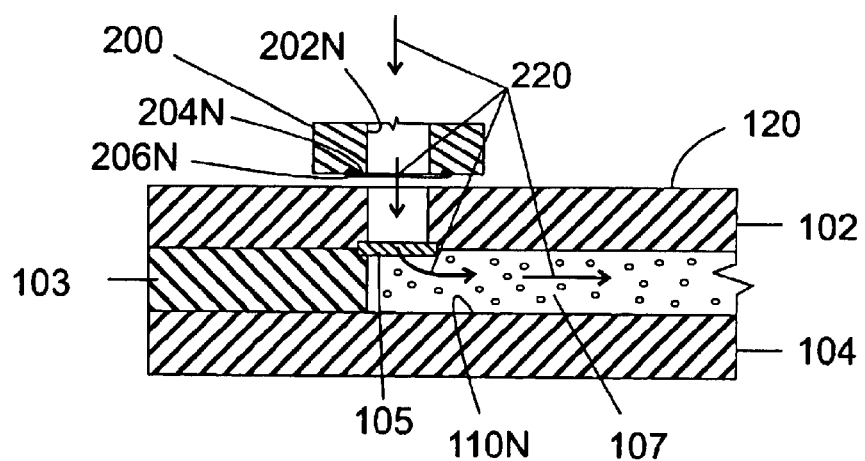
FIG._1B

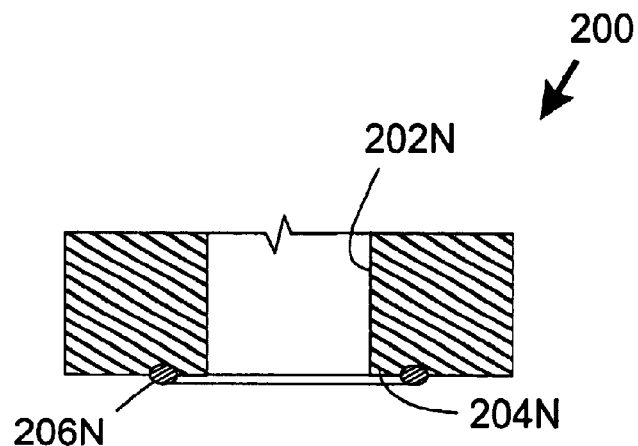
FIG._1C
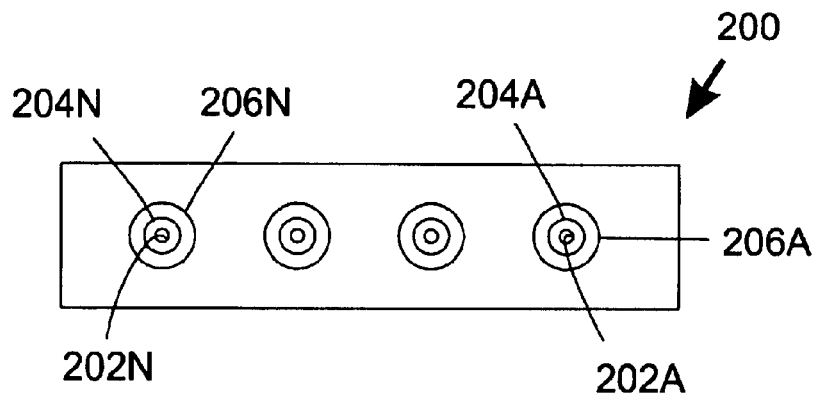
FIG._1D
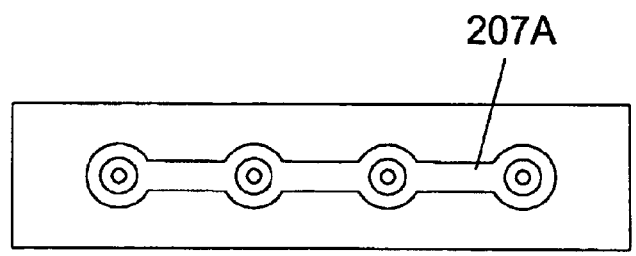
FIG._1E

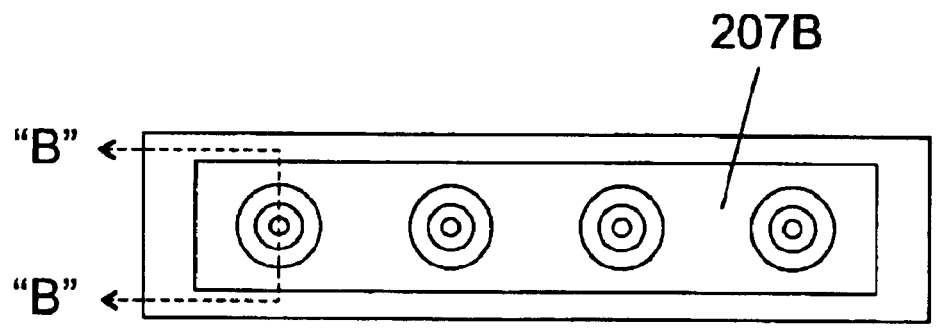
FIG._1F
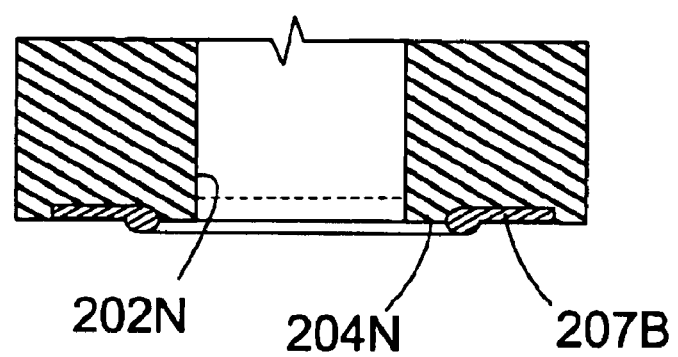
FIG._1G

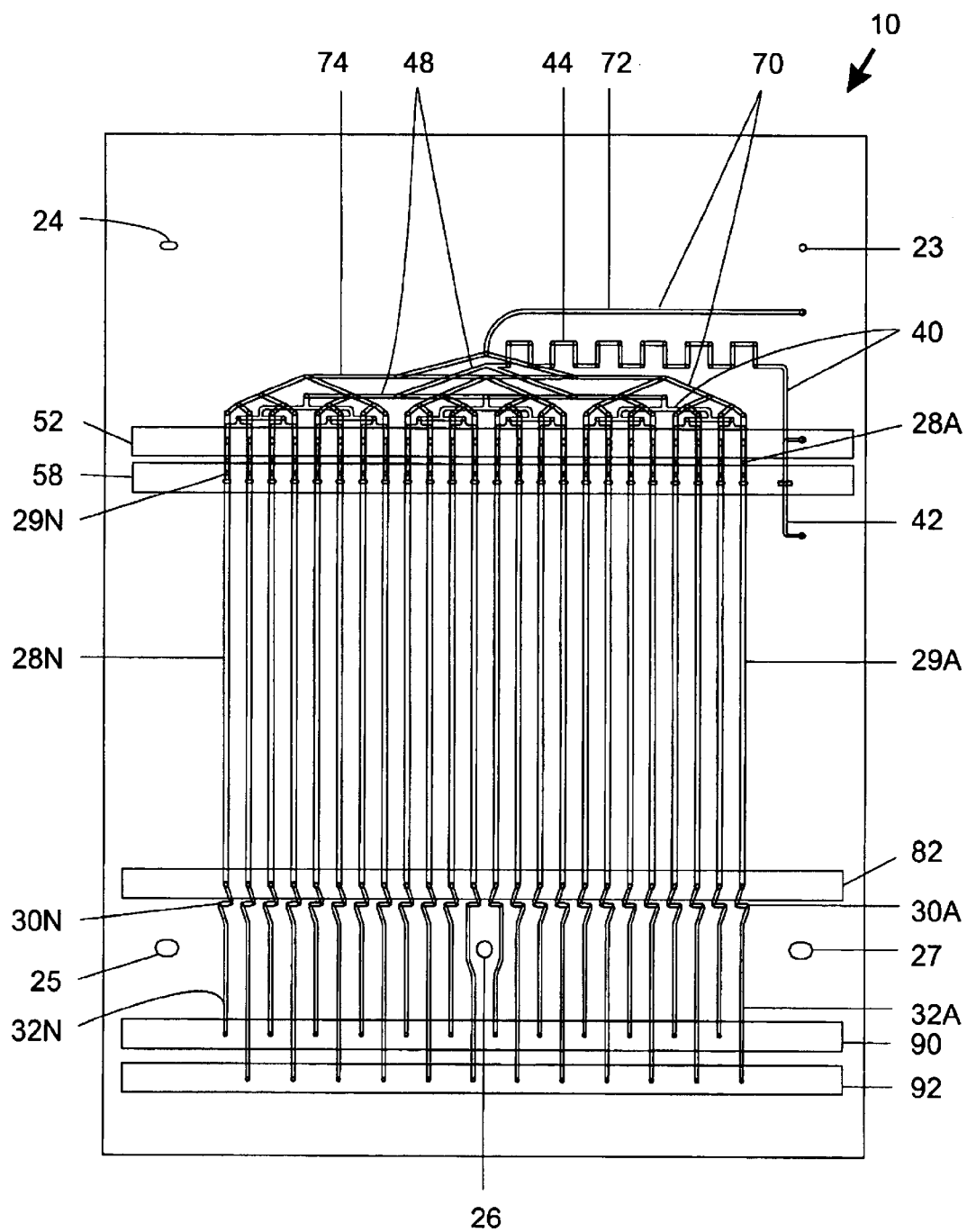
FIG._2

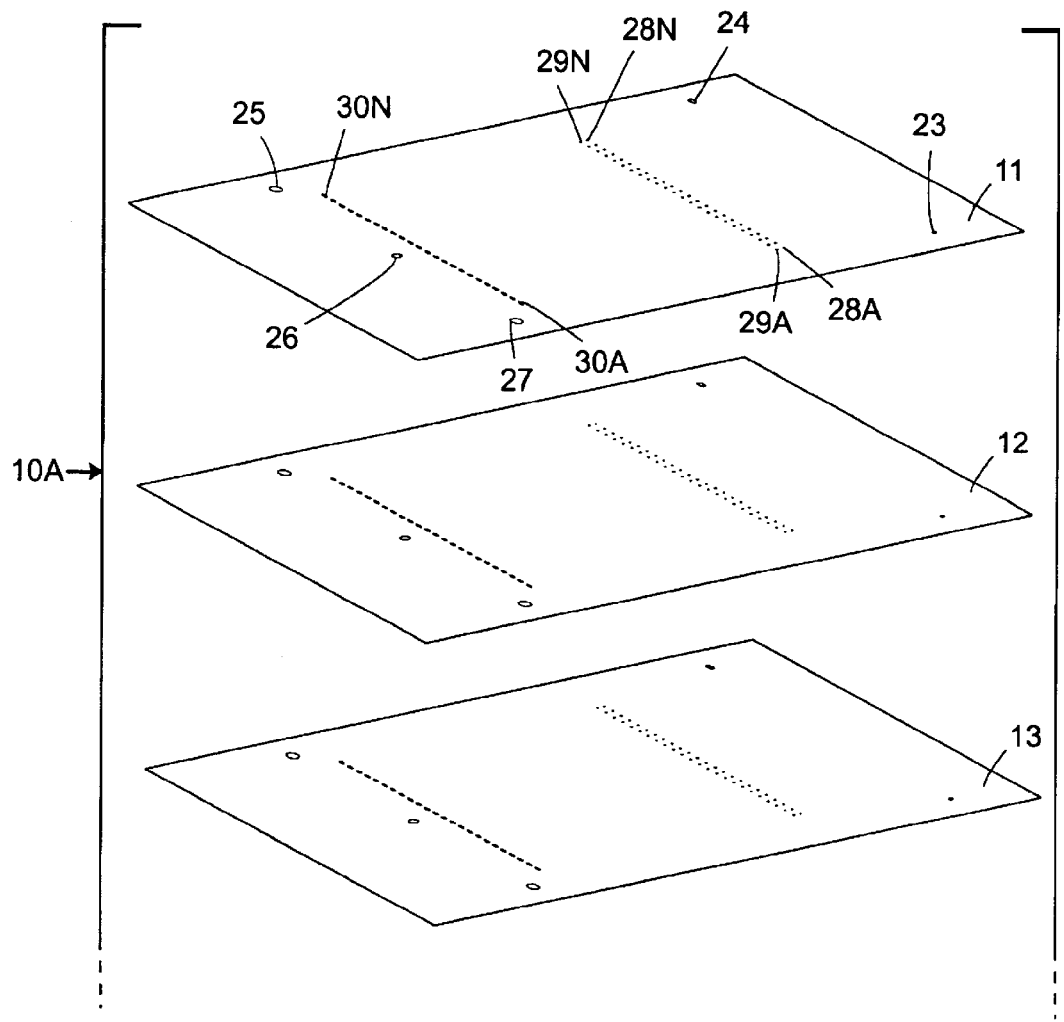
FIG._3A

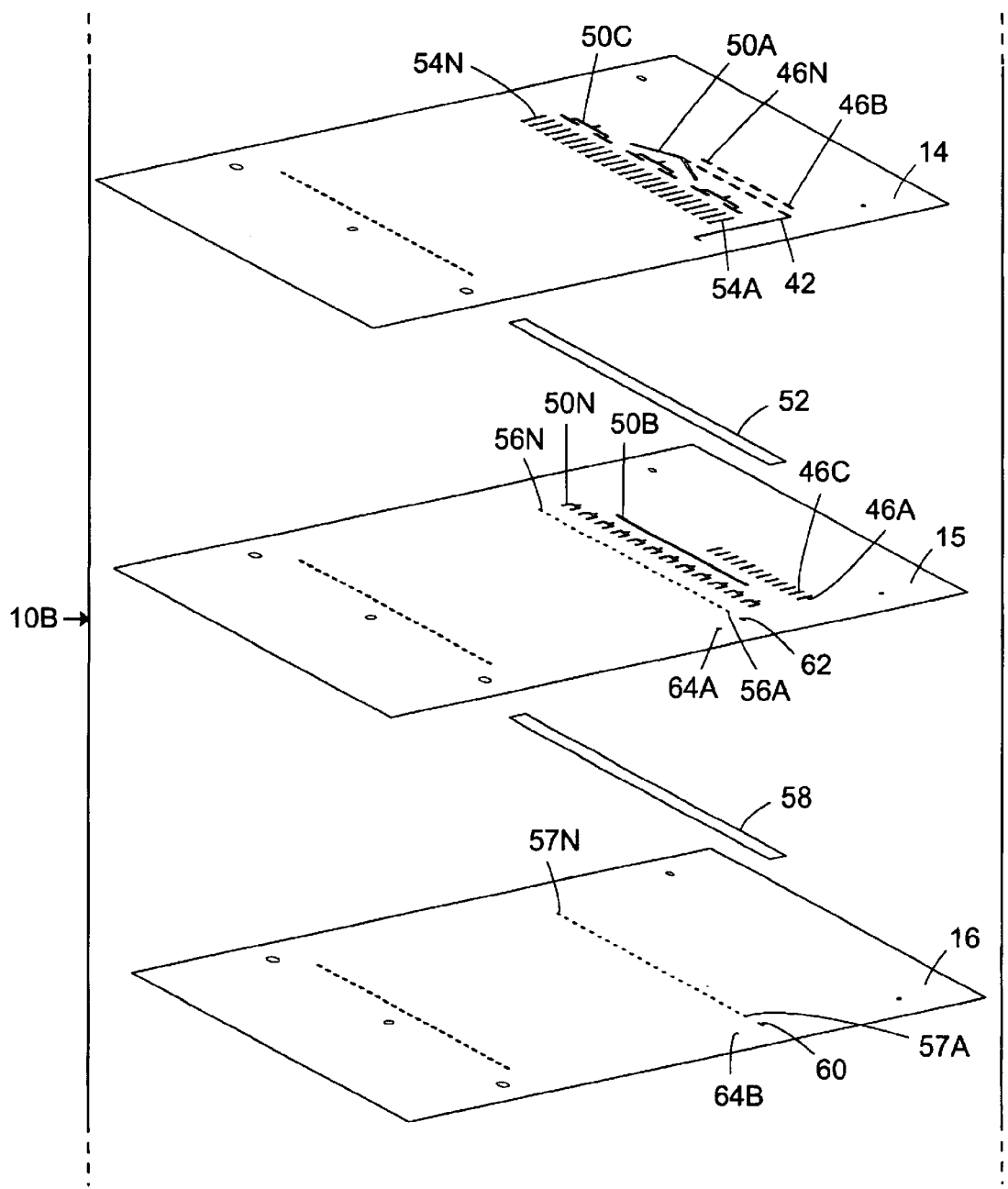
FIG._3B

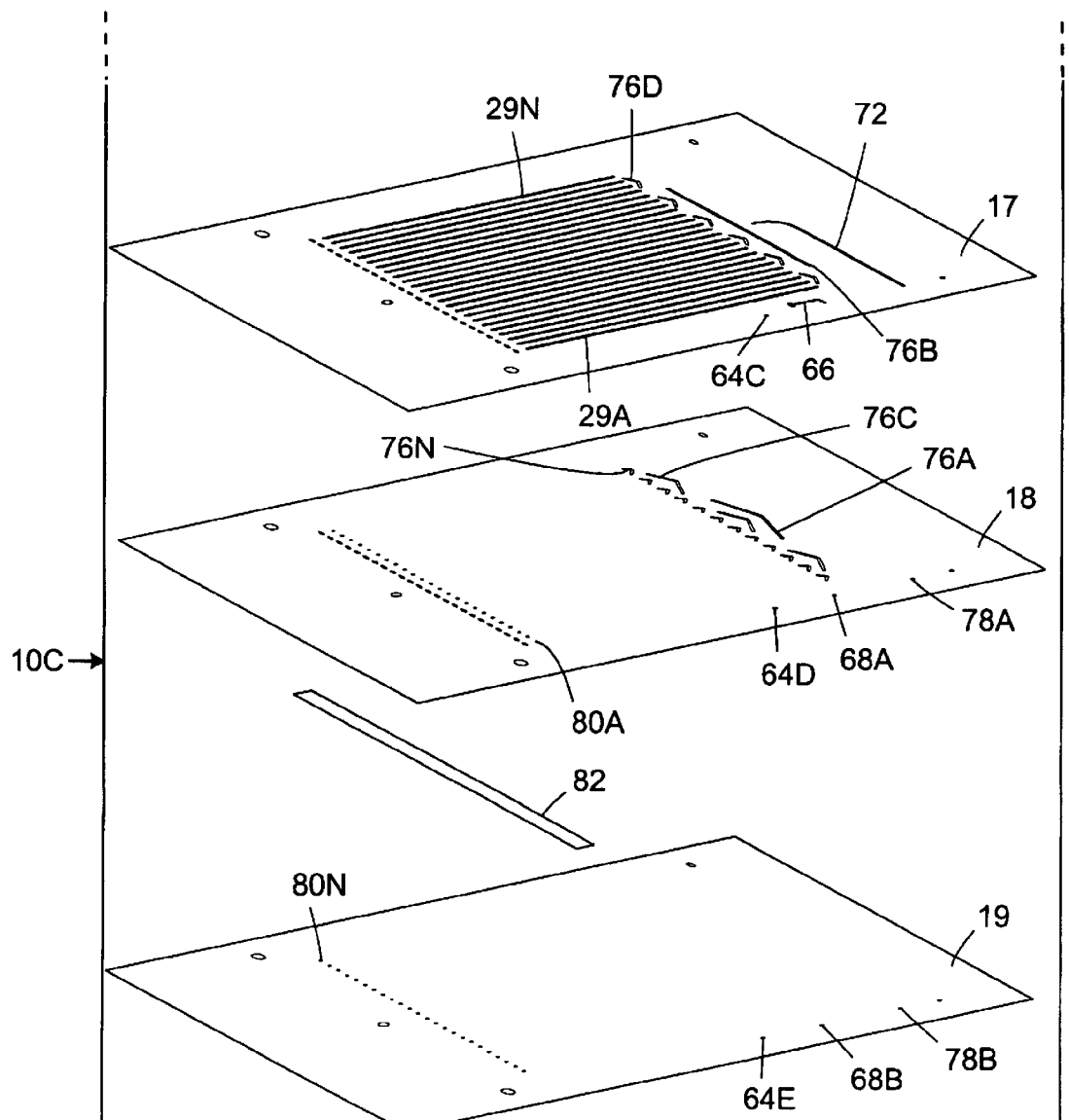
FIG._3C

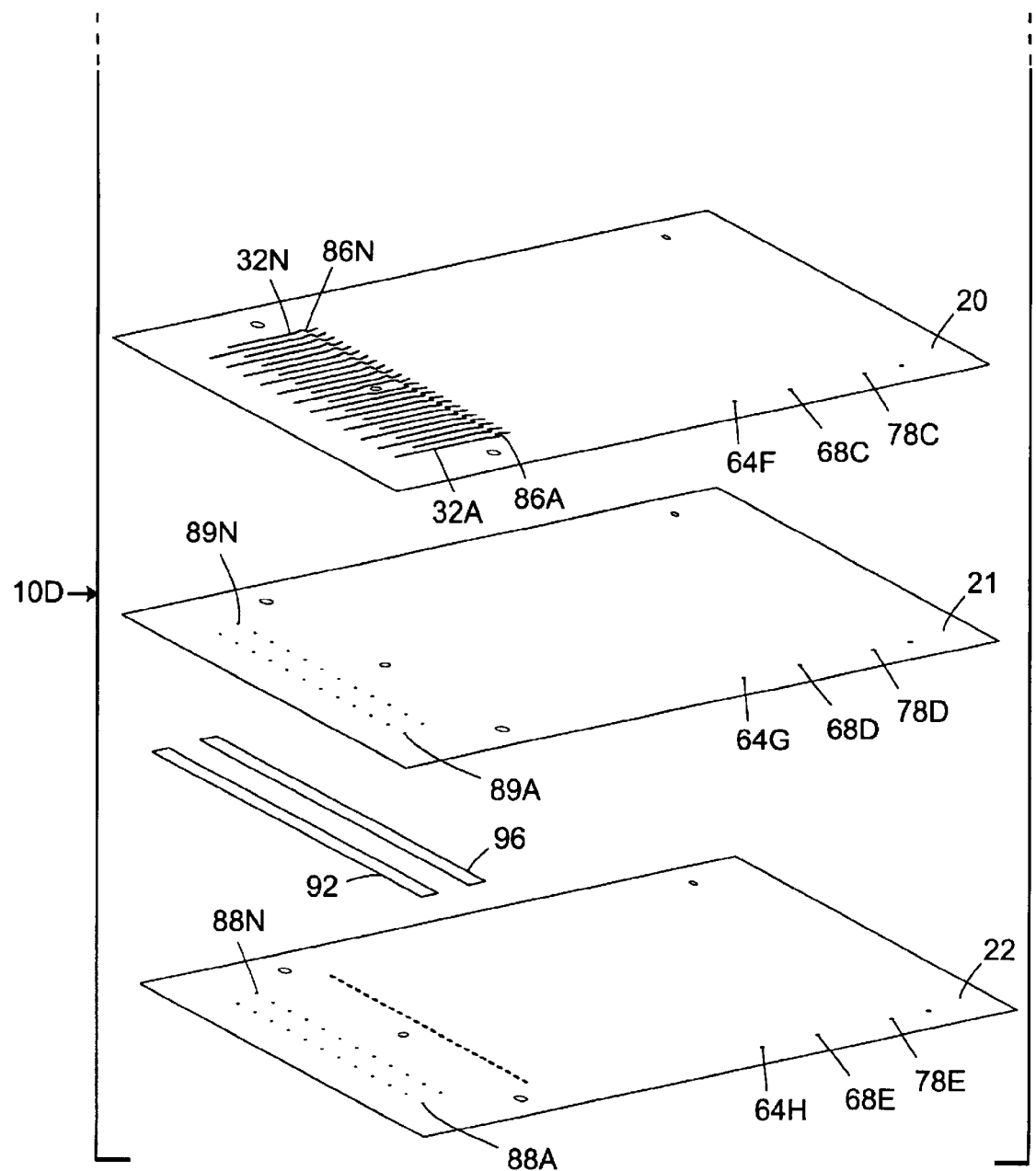
FIG._3D

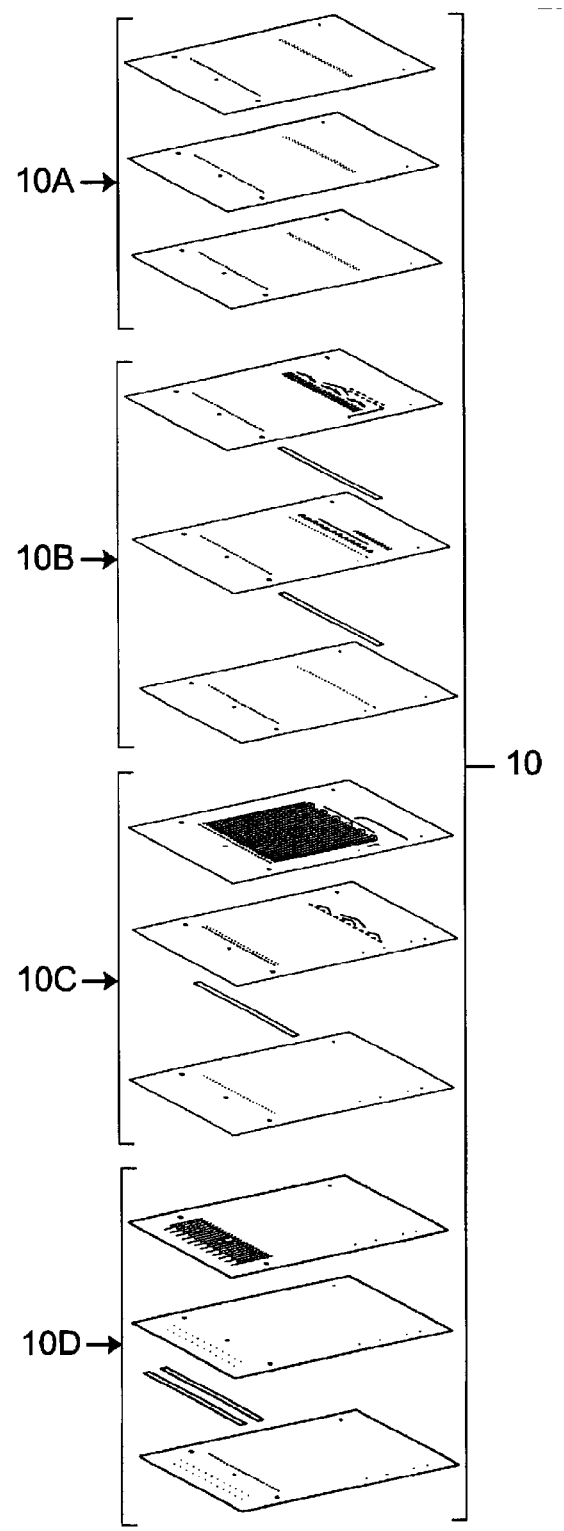
FIG._3E

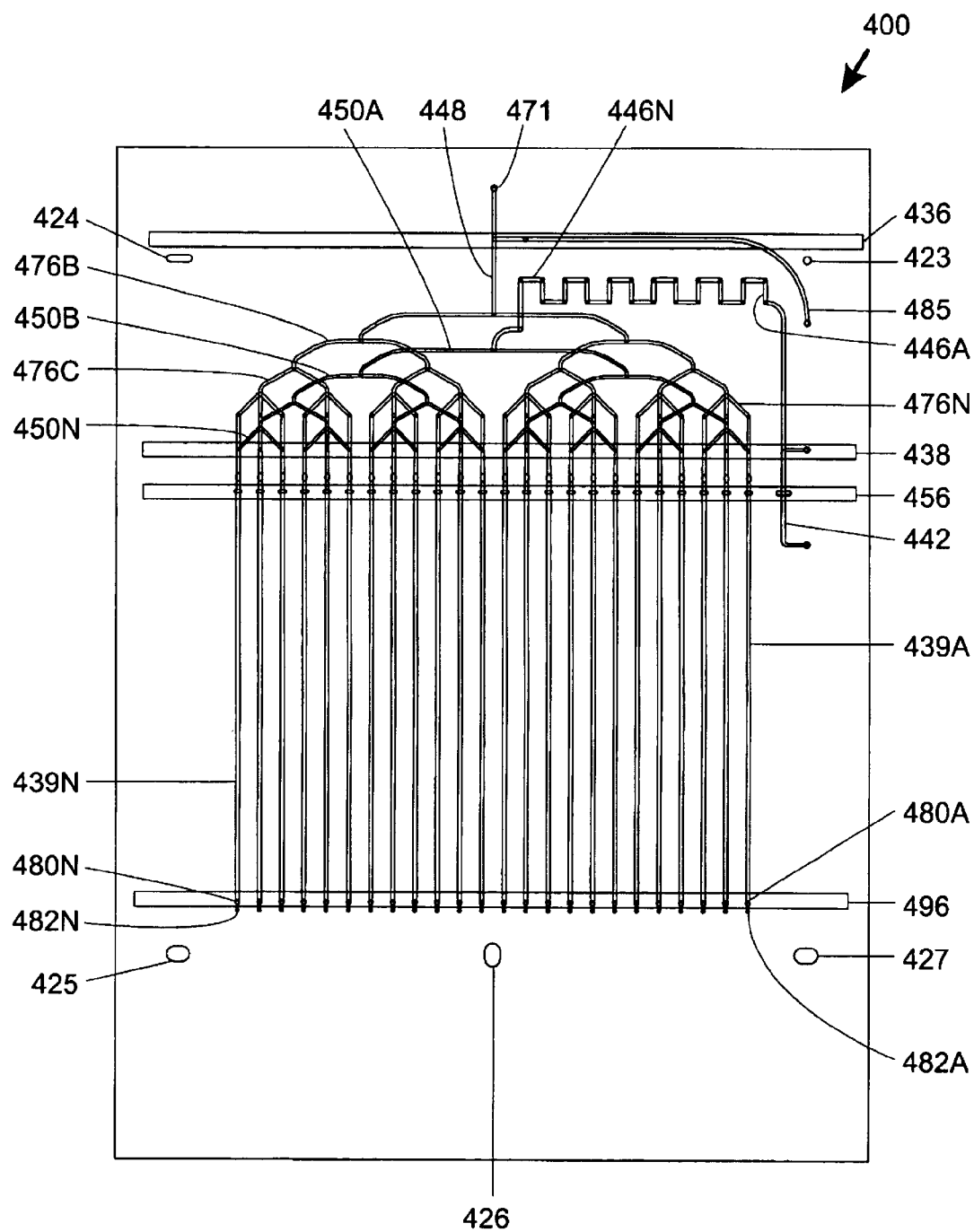
FIG._4

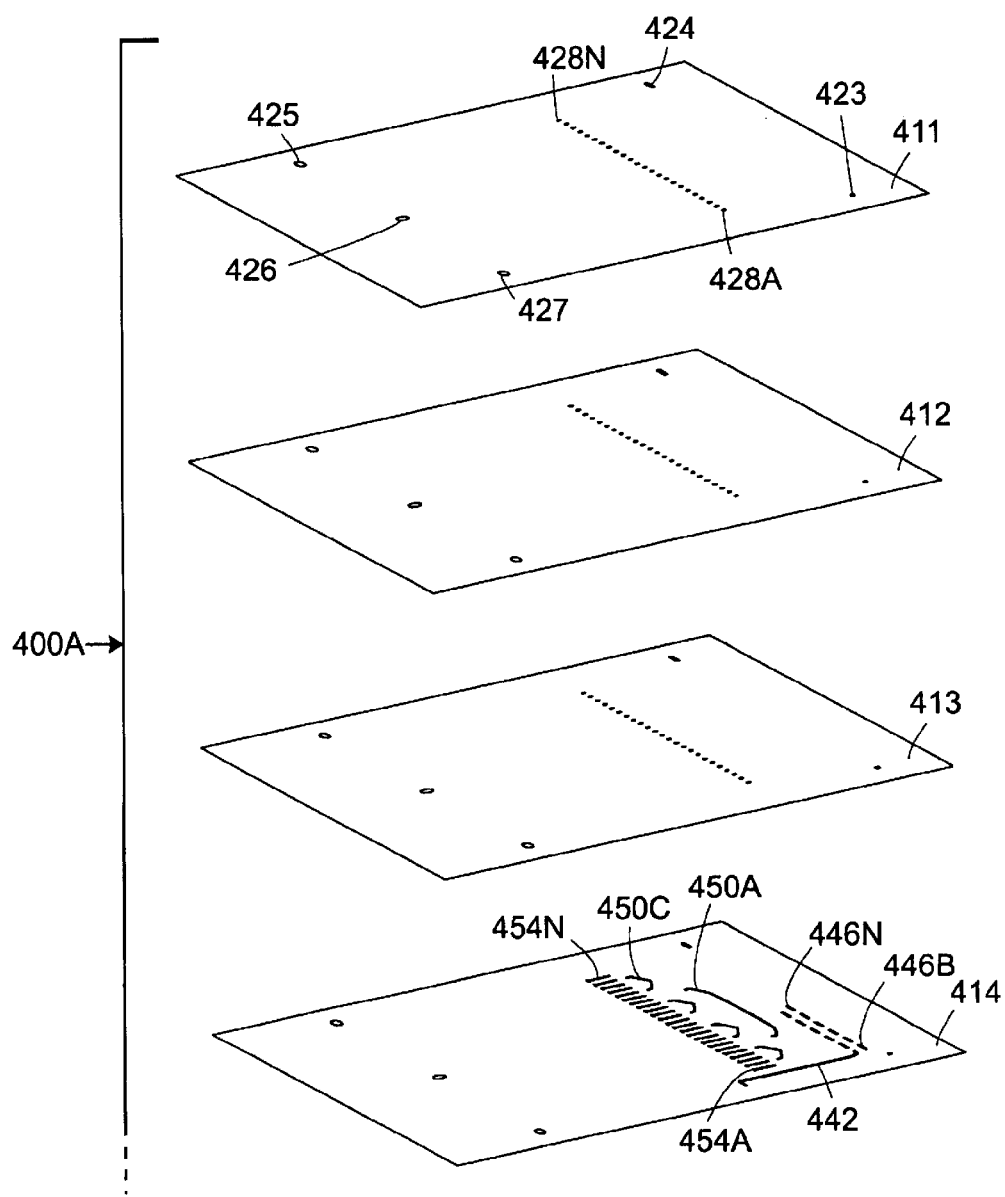
FIG._5A

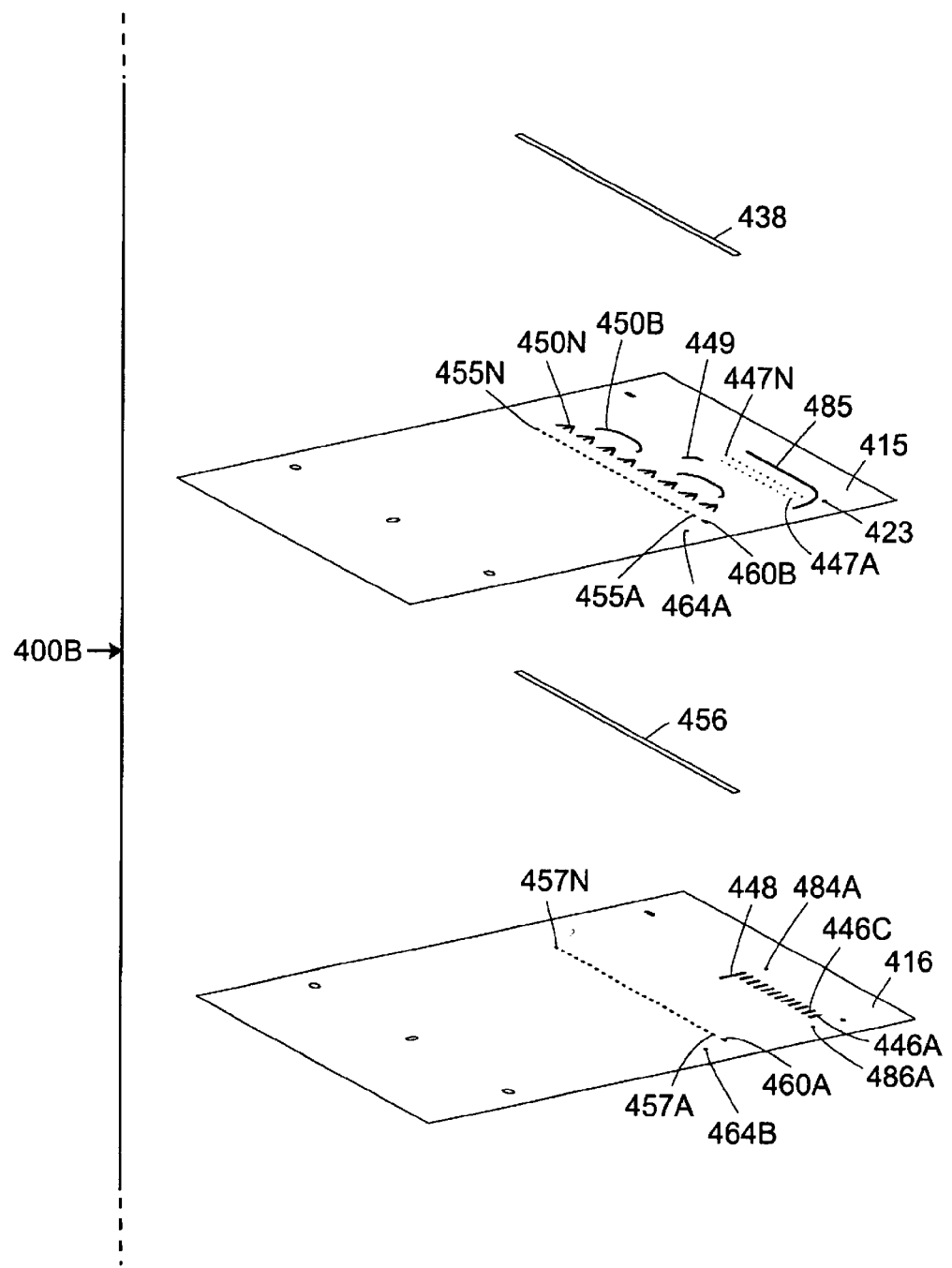
FIG._5B

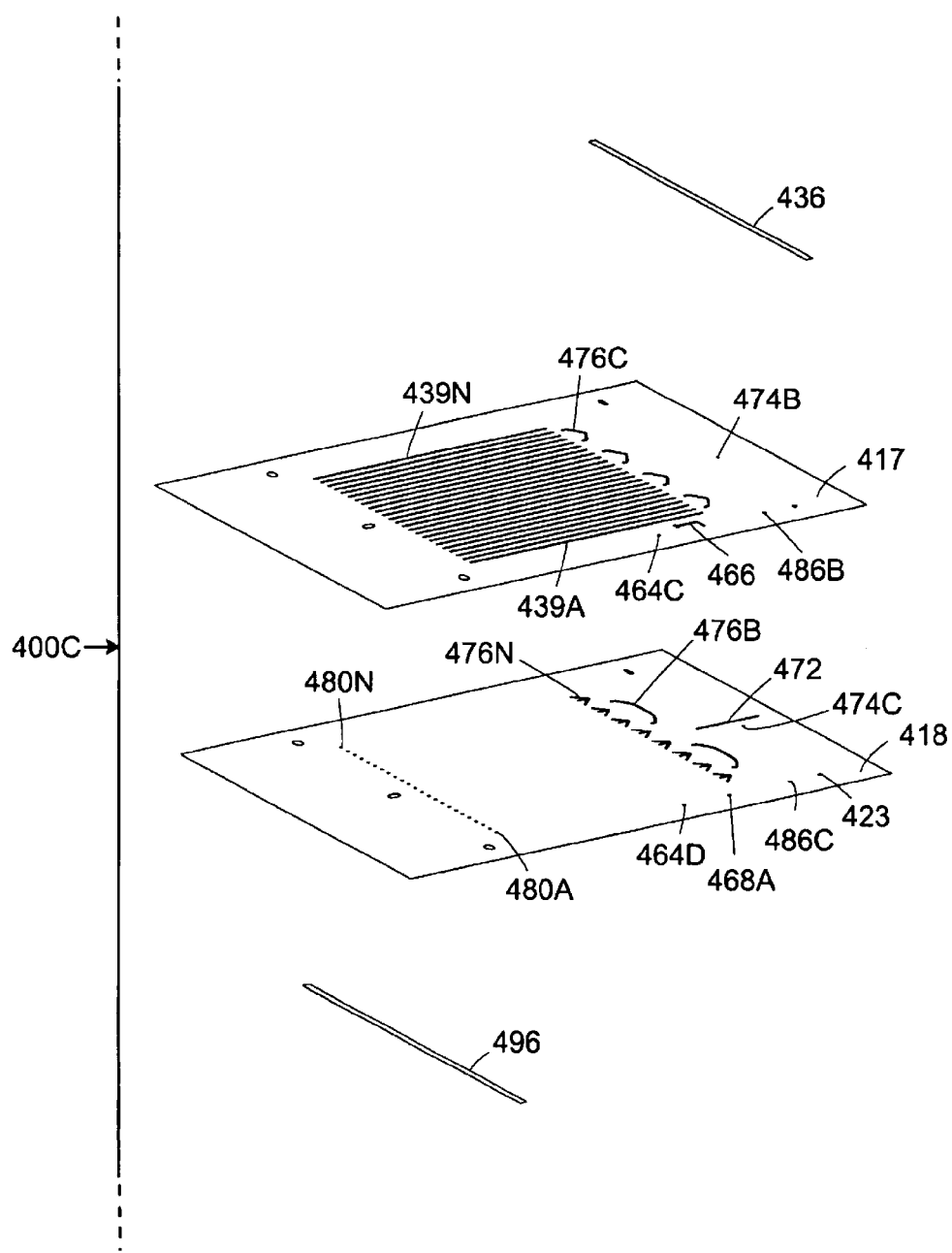
FIG._5C

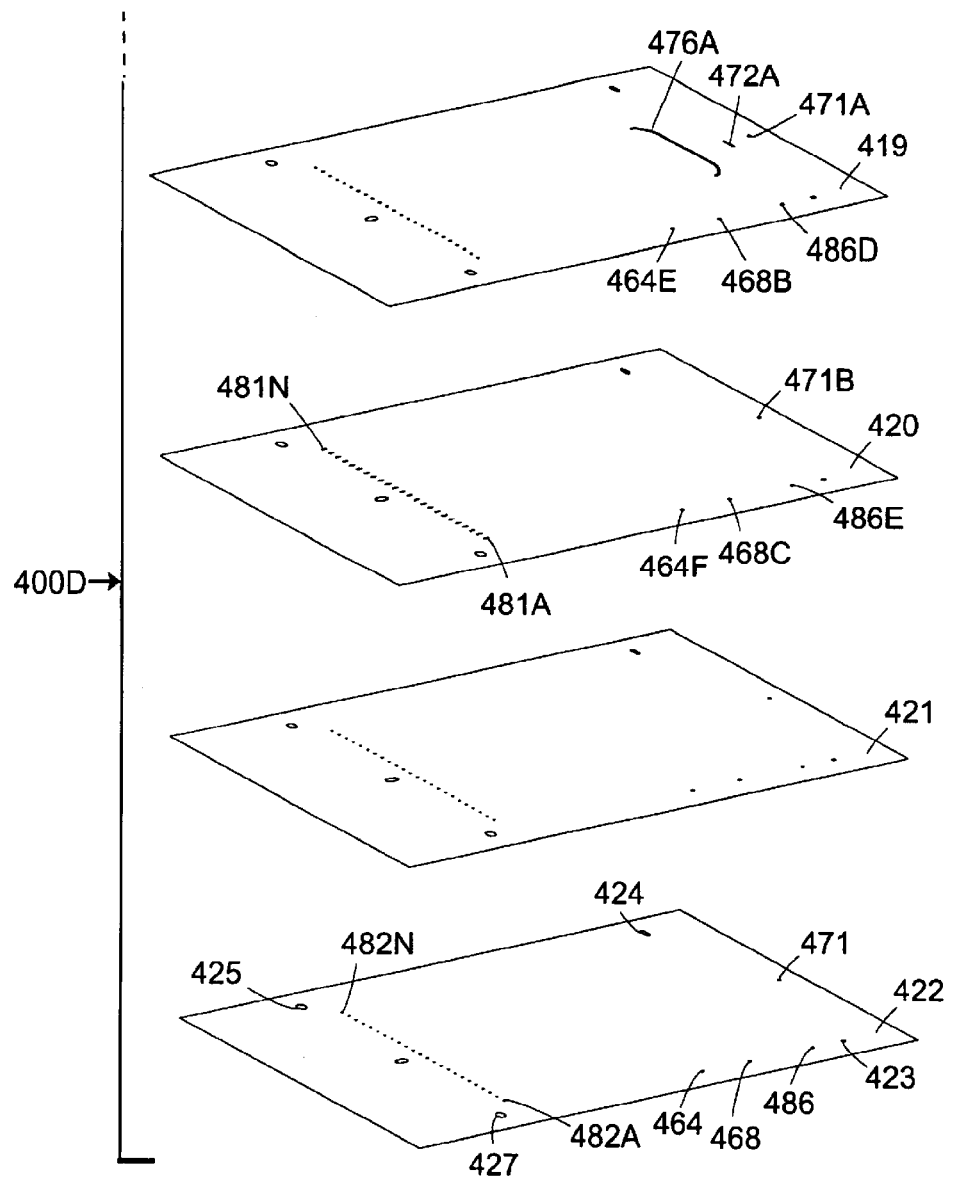
FIG._5D

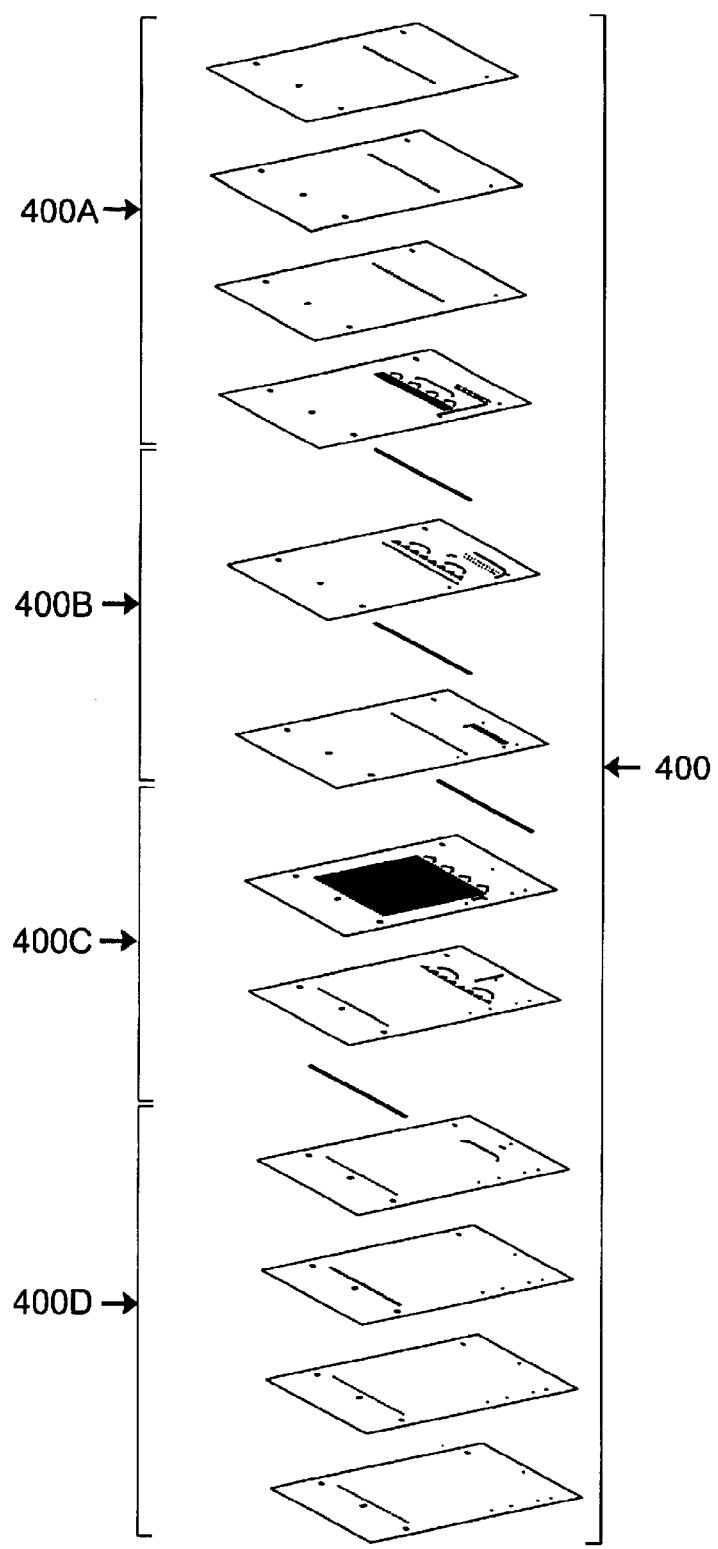
FIG._5E

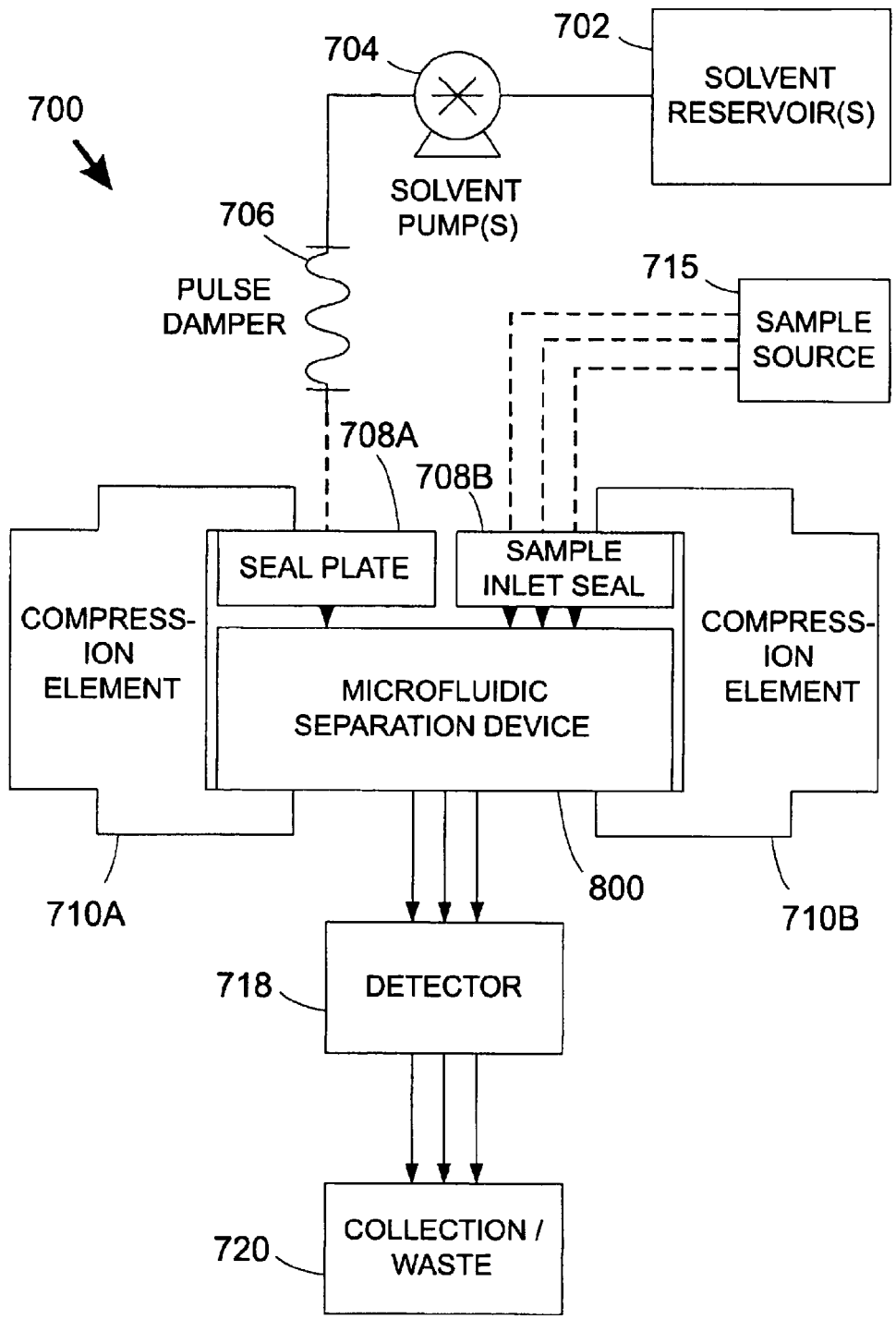
FIG._6

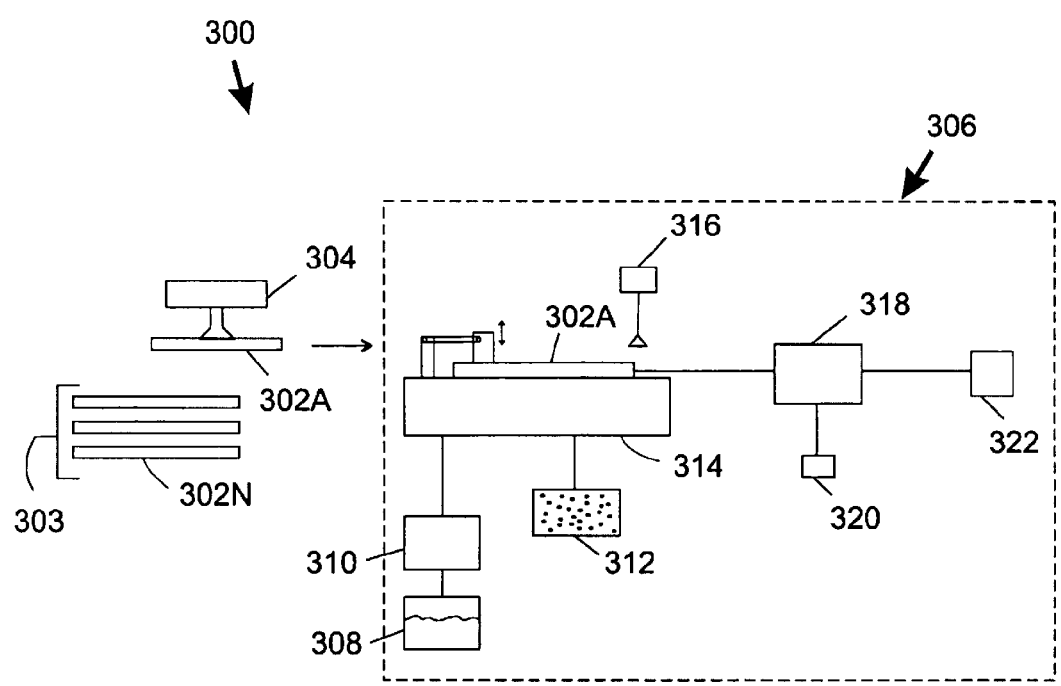
FIG._7A

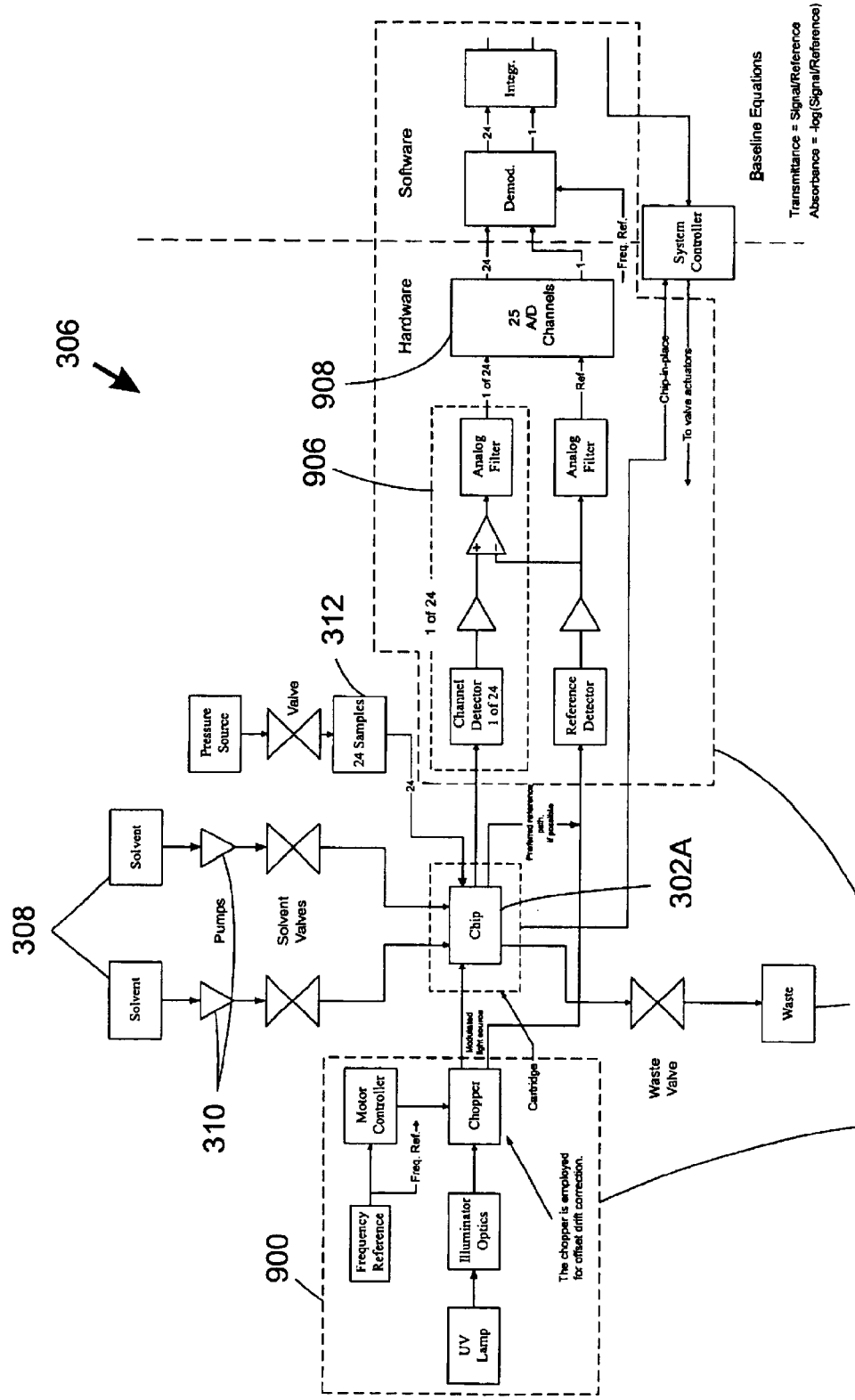
FIG._7B

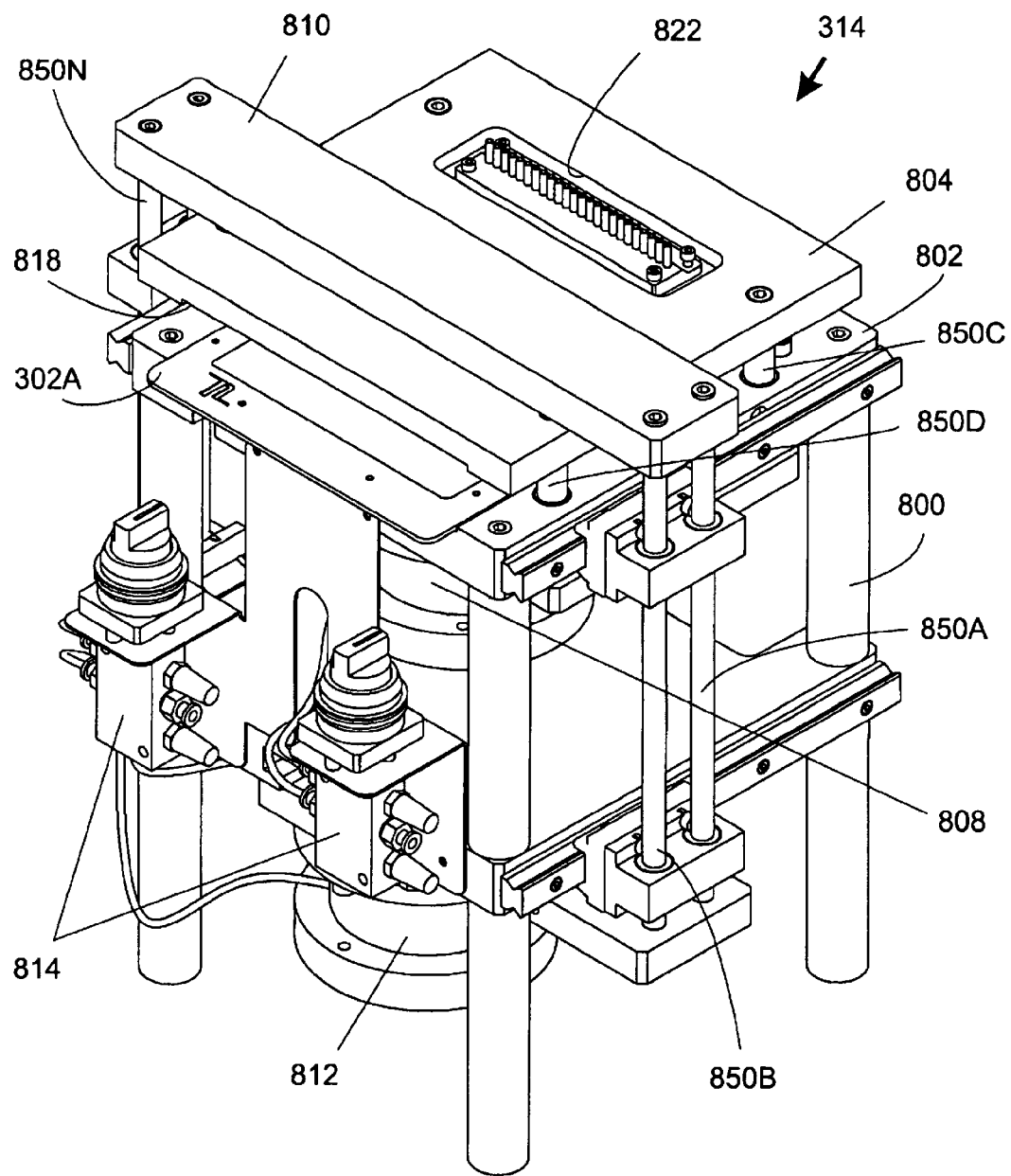
FIG._7D

SYSTEM AND METHOD FOR PERFORMING MULTIPLE PARALLEL CHROMATOGRAPHIC SEPARATIONS

STATEMENT OF RELATED APPLICATIONS

This application claims the benefit of commonly assigned U.S. Provisional Patent Application Ser. No. 60/422,901 filed Oct. 31, 2002 and Ser. No. 60/506,452 filed Sep. 26, 2003, and U.S. Utility patent application Ser. No. 10/649,073 filed Aug. 26, 2003.

FIELD OF THE INVENTION

The present invention relates to the simultaneous performance of multiple chromatographic separations, such as may be used for separating chemical or biological species in parallel.

BACKGROUND OF THE INVENTION

Recent developments in the pharmaceutical industry and combinatorial chemistry have exponentially increased the number of potentially useful compounds, each of which must be characterized (i.e., the components and structure must be understood) in order identify the active components and/or establish processes for synthesizing the compounds. In an effort to increase the speed with which these compounds are analyzed, researchers have sought to introduce a higher degree of automation in the analytical process as well as increase the number of analyses performed in parallel.

One useful analytical process is chromatography, which encompasses a number of methods that are used for separating ions or molecules that are dissolved in or otherwise mixed into a solvent. Liquid chromatography ("LC") is a physical method of separation wherein a liquid "mobile phase" (typically consisting of one or more solvents) carries a sample containing multiple constituents or species through a separation medium or "stationary phase." Various types of mobile phases and stationary phases may be used. Stationary phase material typically includes a liquid-permeable medium such as packed granules (particulate material) disposed within a tube (or other channel boundary). The packed material contained by the tube or similar boundary is commonly referred to as a "separation column." High pressure is often used to obtain a close-packed column with a minimal void between each particle, since better resolution during use is typically obtained from more tightly packed columns. As an alternative to packed particulate material, a porous monolith or similar matrix may be used. So-called "high performance liquid chromatography" ("HPLC") refers to efficient separation methods that are typically performed at high operating pressures.

Typical interactions between stationary phases and solutes include adsorption, ion-exchange, partitioning, and size exclusion. Examples of types of stationary phases to support such interactions are solids, ionic groups on a resin, liquids on an inert solid support, and porous or semi-porous inert particles, respectively. Commonly employed base materials include silica, alumina, zirconium, or polymeric materials. A stationary phase material may act as a sieve to perform simple size exclusion chromatography, or the stationary phase may include functional groups (e.g., chemical groups) to perform other (e.g., adsorption or ion exchange separation) techniques.

Mobile phase is forced through the stationary phase using means such as, for example, one or more pumps, gravity, voltage-driven electrokinetic flow, or other established means for generating a pressure differential. After sample is injected into the mobile phase, such as with a conventional loop valve, components of the sample will migrate according to interactions with the stationary phase and the flow of such components are retarded to varying degrees. Individual sample components may reside for some time in the stationary phase (where their velocity is essentially zero) until conditions (e.g., a change in solvent concentration) permit a component to emerge from the column with the mobile phase. In other words, as the sample travels through voids or pores in the stationary phase, the sample may be separated into its constituent species due to the attraction of the species to the stationary phase. The time a particular constituent spends in the stationary phase relative to the fraction of time it spends in the mobile phase will determine its velocity through the column. Following separation in an LC column, the eluate stream contains series of regions having an elevated concentration of individual component species. Thus, HPLC acts to provide relatively pure and discrete samples of each of the components of a compound. Gradient separations using conventional HPLC systems are typically performed within intervals of roughly five to ten minutes, followed by a flush or rinse cycle before another sample is separated in the same separation column.

Following chromatographic separation in the column, the resulting eluate stream (consisting of mobile phase and sample) contains a series of regions having elevated concentrations of individual species, which can be detected by various flow-through techniques including spectrophotometric (e.g., UV-Vis), fluorimetric, refractive index, electrochemical, or radioactivity detection. Liquid chromatography with flow-through detection generally provides signal response that is proportional to analyte amount or concentration.

Because liquid chromatography is useful in separating, identifying, purifying, and quantifying compounds within various mixtures, it would be desirable to perform multiple chromatographic separations simultaneously. By increasing the number of separations performed in parallel, researchers and scientists may increase the rate at which compounds of interest are isolated and characterized. Nonetheless, the ability to perform multiple parallel separations has been limited for a variety of reasons.

Typically, separation columns used for high performance liquid chromatography (HPLC) are contained in tubes made from high strength materials (to withstand the high pressures that are required by the separation process). Such a tube contains packed particulate stationary phase material, which is retained within the tube by porous "frits" (typically, small coin-shaped pieces of sintered metal or silica) positioned at both ends of the tube. The frits (and the stationary phase) are retained by ferrules and nuts or other appropriate fasteners. One drawback of this type of separation column is the complex and time-consuming fabrication process required to assemble the column.

Another drawback to using conventional separation columns for high-throughput applications is that they must interface with other components of the system through complex fittings, frequently requiring input and output lines to be screwed on to the column. As a consequence of these complex configurations, performing multiple separations in parallel becomes increasingly complex with the addition of each new column to be operated. Moreover, automation of such devices also is challenging, requiring automated systems capable of performing complex tasks such as precisely aligning components and rotating screw fittings.

For example, PCT Patent Application No. WO 02/28509 by Strand et al. ("Strand") discloses a fluid separation conduit cartridge that includes a conventional separation column curved into a "U" shape and encased in a cartridge housing. While the cartridge according to Strand appears to avoid the need for threaded connectors between the cartridge and the instrument, its use of conventional separation column technology still requires complex fabrication operations and numerous parts, such as the ferrule sub-assemblies illustrated in FIGS. 4–7 therein. Moreover, the U-shaped separation column may be undesirable, as fluid flowing along one side of the separation column will have a different path length than fluid flowing along the other side, which may result in peak spreading or other inaccuracies in analytical results. Finally, the cartridge disclosed in Strand includes only one separation column. Presumably, multiple such cartridges could be used on one instrument; however, the removal and replacement of a large number of cartridges, together with management of cartridge re-use, would be time consuming and complex. Presumably, multiple U-shaped separation columns could be included in one cartridge; however, given the nature of this separation column (i.e., conventional design with threaded fitting to retain the stationary phase material), such a cartridge would be large and bulky, eliminating one of the principal advantages of microfluidic operations—small instrument footprint.

In another example, PCT Patent Application No. WO 01/09598 by Holl et al. ("Holl") discloses a manifold for providing fluids to a microfluidic de-gassing device. The manifold according to Holl clamps onto a microfluidic device, pressing the protruding end of an interconnect tube into an elastomeric layer on the surface of and surrounding the inlet orifice of the microfluidic device. The system disclosed therein has the disadvantage of requiring an elastomeric layer to be added to the surface of the microfluidic device, the bonding of which layer may be problematic depending on the materials used for the elastomeric layer and the device. For instance, if an adhesive is used to bond the elastomeric layer to the surface of this device, the adhesive may contaminate the samples introduced into the microfluidic device. Adhesiveless bonding methods may limit the materials that may be used for the microfluidic device and elastomeric layer, potentially limiting the types of compatible fluids that may be used in the device. Also, if the elastomeric layer should be damaged, the entire microfluidic device must be repaired or replaced, potential interrupting operations. Moreover, the interconnect system disclosed by Holl requires precise placement of the interconnect tube with respect to the surface of the manifold to ensure that the interconnect tube protrudes a limited distance into the elastomeric layer. This is particularly important as Holl notes that excessive intrusion of an interconnect tube into an elastomeric layer may cause the elastomeric layer to bulge inward into the orifice, thereby occluding the orifice and preventing the flow of fluid through the interface. Finally, the interface disclosed by Holl is intended for use in degassing—an application typically not involving pressures significantly greater than about 50 psi. In contrast, pressures associated with liquid chromatography and HPLC in particular, typically exceed about 100 psi, often exceeding about 200 psi, about 300 psi and even as much as about 500 psi.

Thus, it would be desirable to provide a system for performing multiple liquid chromatography separations in parallel where multiple separation columns may be easily installed within and operated with the system. It also would be desirable to provide a microfluidic interface capable of maintaining a seal at the high operating pressures typically associated with liquid chromatography.

BRIEF DESCRIPTION OF THE DRAWINGS

FIG. 1A is a perspective view of a multi-column microfluidic separation device and a device interface.

FIG. 1B partial cross-section of the device and interface of FIG. 1A taken along section line "A"—"A".

FIG. 1C is an enlarged cross section of the interface shown in FIG. 1B.

FIG. 1D is a bottom view interface shown in FIG. 1A.

FIG. 1E is a bottom view of a first alternative interface embodiment suitable for use with the separation device of FIGS. 1A–1B.

FIG. 1F is a bottom view of a second alternative interface embodiment suitable for use with the separation device of FIGS. 1A–1B.

FIG. 1G partial cross-section of the interface of FIG. 1F taken along section line "B"—"B".

FIG. 2 is a top view of a twenty-four column, twelve-layer microfluidic separation device.

FIG. 3A is an exploded perspective view of a first portion, including the first through third layers, of the device shown in FIG. 2.

FIG. 3B is an exploded perspective view of a second portion, including the fourth through sixth layers, of the device shown in FIG. 2.

FIG. 3C is an exploded perspective view of a third portion, including the seventh through ninth layers, of the device shown in FIG. 2.

FIG. 3D is an exploded perspective view of a fourth portion, including the tenth through twelfth layers, of the device shown in FIG. 2.

FIG. 3E is a reduced scale composite of FIGS. 3A–3D showing an exploded perspective view of the device of FIG. 2.

FIG. 4 is a top view of a multi-layer microfluidic device containing twenty-four separation columns suitable for performing pressure-driven liquid chromatography.

FIG. 5A is an exploded perspective view of a first portion, including the first through fourth layers, of the microfluidic device shown in FIG. 4.

FIG. 5B is an exploded perspective view of a second portion, including the fifth and sixth layers, of the microfluidic device shown in FIG. 4.

FIG. 5C is an exploded perspective view of a third portion, including the seventh and eighth layers, of the microfluidic device shown in FIG. 4.

FIG. 5D is an exploded perspective view of a fourth portion, including the ninth through twelfth layers, of the microfluidic device shown in FIG. 4.

FIG. 5E is a reduced size composite of FIGS. 5A–5D showing an exploded perspective view of the microfluidic device of FIG. 4.

FIG. 6 is a schematic of a system for performing high throughput pressure-driven liquid chromatography utilizing a microfluidic device having a plastically deformable outer layer.

FIG. 7A is a schematic illustration of a system for simultaneously performing multiple separations.

FIG. 7B is a schematic illustration of the instrument portion of the system of FIG. 7A.

FIG. 7D is a perspective view of the device interface portion of the system of FIG. 7A.

Figure 7C:
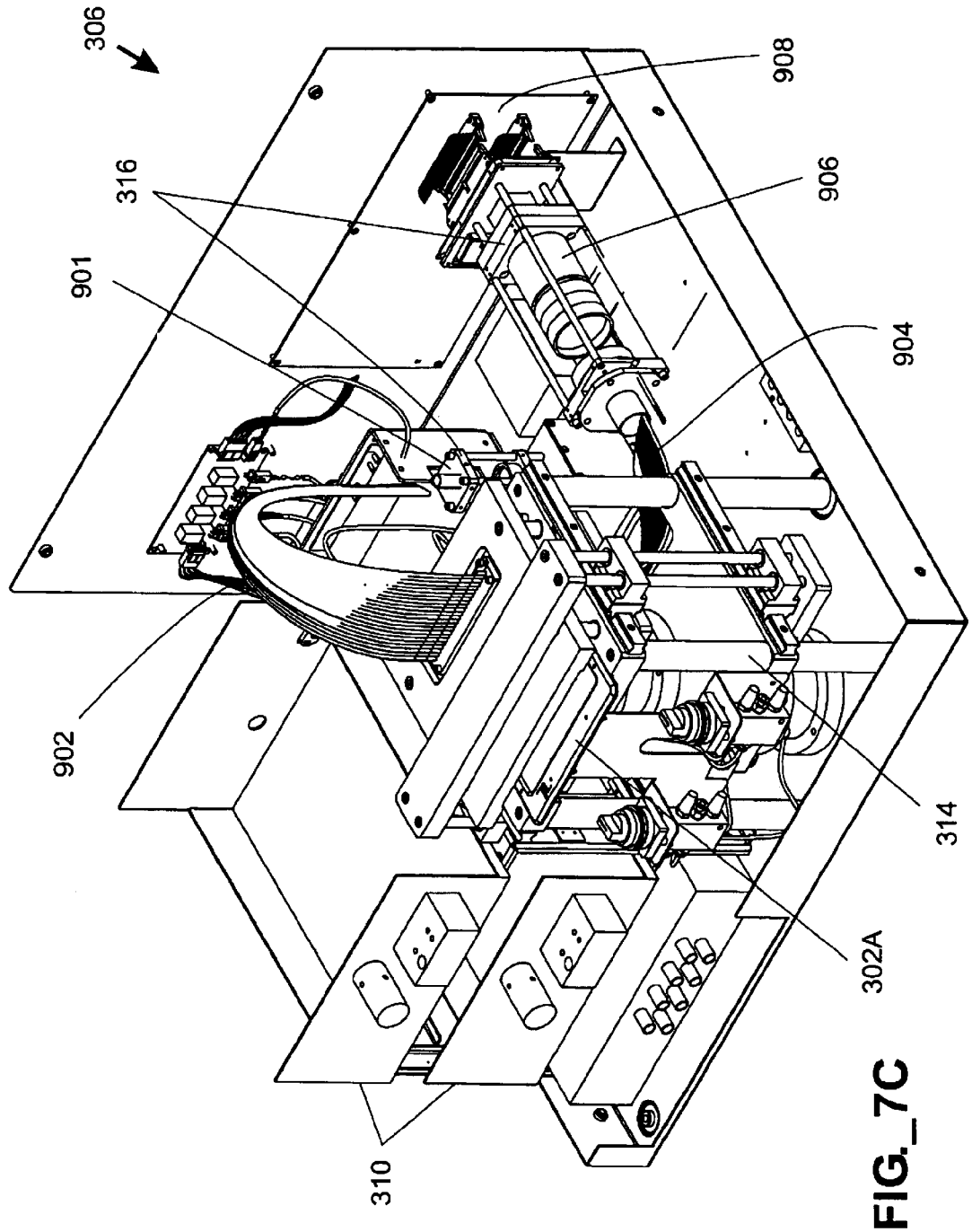
FIG. 7C is a perspective view of the instrument portion of the system of FIG. 7A.

None of the figures are drawn to scale unless indicated otherwise. The size of one figure relative to another is not intended to be limiting, since certain figures and/or features may be expanded to promote clarity in the description.

DETAILED DESCRIPTION OF PREFERRED EMBODIMENTS OF THE INVENTION

Definitions

The terms "column" or "separation column" as used herein are used interchangeably and refer to a region of a fluidic device that contains stationary phase material and is adapted to perform a separation process.

The term "fluidic distribution network" refers to an interconnected, branched group of channels and/or conduits capable of adapted to divide a fluid stream into multiple substreams.

The term "frit" refers to a liquid-permeable material adapted to retain stationary phase material within a separation column.

The term "microfluidic" as used herein refers to structures or devices through which one or more fluids are capable of being passed or directed and having at least one dimension less than about 500 microns.

The term "packed" as used herein refers to the state of being substantially filled with a packing material (such as a particulate material).

The term "parallel" as used herein refers to the ability to concomitantly or substantially concurrently process two or more separate fluid volumes, and does not necessarily refer to a specific channel or chamber structure or layout.

The term "plurality" as used herein refers to a quantity of two or more.

The term "slurry" as used herein refers to a mixture of particulate matter and a solvent, preferably a suspension of particles in a solvent.

The term "stencil" as used herein refers to a material layer or sheet that is preferably substantially planar through which one or more variously shaped and oriented portions have been cut or otherwise removed through the entire thickness of the layer, and that permits substantial fluid movement within the layer (e.g., in the form of channels or chambers, as opposed to simple through-holes for transmitting fluid through one layer to another layer). The outlines of the cut or otherwise removed portions form the lateral boundaries of microstructures that are formed when a stencil is sandwiched between other layers such as substrates and/or other stencils.

Fluidic Devices Generally

Traditionally, microfluidic devices have been fabricated from rigid materials such as silicon or glass substrates using surface micromachining techniques to define open channels and then affixing a cover to a channel-defining substrate to enclose the channels. There now exist a number of well-established techniques for fabricating microfluidic devices, including machining, micromachining (including, for example, photolithographic wet or dry etching), micromolding, LIGA, soft lithography, embossing, stamping, surface deposition, and/or combinations thereof to define apertures, channels or chambers in one or more surfaces of a material or that penetrate through a material.

A preferred method for constructing microfluidic devices utilizes stencil fabrication, which includes the lamination of at least three device layers including at least one stencil layer or sheet defining one or more microfluidic channels and/or other microstructures. As noted previously, a stencil layer is preferably substantially planar and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Various preferred embodiments utilize porous materials including filtration media. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties. For instance, particularly desirable polymers include polyolefins, more specifically polypropylenes, and vinyl-based polymers.

Various means may be used to seal or bond layers of a device together. For example, adhesives may be used. In one embodiment, one or more layers of a device may be fabricated from single- or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied.

Device layers may be directly bonded without using adhesives to provide high bond strength (which is especially desirable for high-pressure applications) and eliminate potential compatibility problems between such adhesives and solvents and/or samples. For example, in one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Preferred Fluidic Devices

One advantage of performing chromatography in a microfluidic format is that multiple separations can be performed in parallel with a single chromatography system. If multiple columns are provided in a single separation device, then such a device preferably has at least one associated fluidic distribution network to permit operation with a minimum number of expensive (typically external) system components such as pumps and pulse dampers. One example of a multi-column microfluidic separation device suitable for performing pressure-driven liquid chromatography is provided in FIGS. 1A–1C, a multi-column microfluidic device 100 has a plurality of separation columns 110A–110N. (Although FIGS. 1A–1B show the device 100 having four columns 110A–110N, it will be readily apparent to one skilled in the art that any number of columns 110A–110N may be provided. For this reason, the designation "N" is used to represent the last column 110N, with the understanding that "N" represents a variable and could represent any desired number of columns. This convention is used throughout this document.) Each column 110A–110N has an inlet port 113A–113N and an outlet port 114A–114N. The device 100 is made with three device layers 102–104, one of which is a stencil layer 103 that defines the lateral boundaries of the separation columns 110A–110N. The first layer 102 defines the inlet ports 113A–113N and outlet ports 114A–114N and further serves as the "ceiling" of the separation columns 110A–110N. The third layer 104 defines the "floor" of the separation columns 110A–110N. The device 100 also includes frits 105, 106 disposed between the first layer 102 and the stencil layer 103. The frits 105, 106 retain a stationary phase 107 (typically a packed particulate) within the columns 110A–110N. The columns 110A–110N may be packed prior to assembly, or, optionally, packed through individual packing channels 111A–111N or through a manifold system (not shown) such as that described below with reference to the device 10.

In operation, samples and mobile phase are injected into the device 100 through the inlet ports 113A–113N and (as shown by the flow arrows 220) through the first frit 105 and through the separation columns 110A–110N. After traveling through the columns 110A–110N, the sample streams (now separated into their components) exit the device 100 through the second frit 106 and outlet ports 114A–114N.

In a preferred embodiment, a fluidic interface includes a press-fit interconnect that provides fluid to a microfluidic device at an operating pressure while maintaining a substantially fluid-tight seal. For example, FIGS. 1A–1G show various embodiments of a fluidic interface 200 having a plurality of fluid bores 202A–202N, a plurality of central protrusions 204A–204N and a plurality of O-rings 206A–206N. Such an interface 200 is positioned to abut the device 100 such that the fluid bores 202A–202N coincide with the inlet ports 113A–113N. The central protrusions 204A–204N act to retain the O-rings 206A–206N.

When the fluidic interface 200 is pressed against the device 100, the O-rings 206A–206N are compressed, forming the desired seal. The tips the central protrusions 204A–204N preferably do not contact the outer surface 120 of the device 100, and may be recessed slightly from the plane of the lower surface of the interface 200. Notably, the central protrusions 204A–204N prevent the O-rings 206A–206N from deforming inwardly towards the bores 202A–202N, thereby preventing any inadvertent or undesirable occlusion of the bores 202A–202N by the O-rings 206A–206N. Furthermore, the central protrusions 204A–204N act to retain the O-rings 206A–206N in place, thus obviating the need for adhesives or other bonding methods for retaining the O-rings 206A–206N. Also, because the O-rings 206A–206N are mounted on the interface 200, damaged O-rings 206A–206N may easily be replaced without the need for replacing the microfluidic device 100.

FIGS. 1E–1G illustrate alternate embodiments of a fluidic interface 200. Notably, the O-rings may be incorporated or substituted with a single gasket 207A, 207B, having either a series of interconnected O-rings (207A) or a sheet gasket with raised O-ring segments (207B). Alternatively, the fluidic interface 200 may include a gasketless seal, such as that described in commonly-assigned U.S. patent application Ser. No. 10/649,073, filed Aug. 26, 2003, the entirety of which is incorporated herein by this reference.

It has been found that applying a pressure of about 25–30 psi to the interface 200 (for example, in one embodiment, the interface is integrated with a plate having dimensions of about 6 inches by 6 inches to which a total force of about 1000 pounds is applied) against the device 100 is sufficient to establish a substantially fluid-tight seal capable of withstanding operating pressures in excess of the burst pressure of an adhesivelessly-bonded polypropylene microfluidic device of about 400–500 psi or more.

In tests, O-rings fabricated with silicon were used for separations performed with conventional mobile phases including acetonitrile, water and methanol without significant degradation of the seal or O-ring and with no evidence of contamination of the results of the separation. Other O-ring and device layer materials, such as, but not limited to, ethylene propylene diene monomer (EPDM) or perfluoroelastomers, may be selected as appropriate for particular stationary phases, mobile phases and analytes anticipated to be used with the device.

It will be readily apparent to one skilled in the art that multi-column microfluidic separation devices may include any of the features described above as well as other advantageous features. For instance, such a device is not restricted to providing four separation columns, but may include any desirable number of columns. Also, other functional structures, such as, but not limited to, mixers, fraction collectors, splitters, reaction chambers, and reservoirs, may be included in the device so that more complex analytical procedures may be carried out within the device.

In one embodiment, a microfluidic device 10 includes multiple channels that may be packed to form multiple separation columns. FIGS. 2 and 3A–3E illustrate a microfluidic separation device 10 constructed with twelve layers 11–22, including multiple stencil layers 14, 15, 17, 18, 20. Each of the twelve layers 11–22 defines five alignment holes 23–27, which are used in conjunction with external pins (not shown) to aid in aligning the layers during construction or in aligning the device 10 with an external interface during a packing process or during operation of the device 10.

The first through third layers 11–13 define a plurality of sample ports 28A–28N that permit samples to be introduced to a plurality of separation columns 29A–29N (defined in the seventh device layer 17) and a plurality of optical detection windows 30A–30N. Two sample ports 28A–28N and 29A–29N are associated with each separation column 29A–29N to permit injection of precise volumes or "plugs" of sample into each column 29A–29N. Optical detection windows 30A–30N also are defined in the fourth through eight and twelfth device layers 14–18, 22. The optical detection windows 30A–30N facilitate optical detection by reducing the amount of material between an optical detector (not shown), such as a conventional UV-VIS detector, and the samples contained in output analysis channels 32A–32N (defined in the tenth device layer 20) downstream of the columns 30A–30N.

The fourth through sixth layers 14–16 define a mobile phase distribution network 40 that includes a mobile phase mixing channel 42, a composite mixing channel 44 (made up of a plurality of mixer segments 46A–46N) and a mobile phase splitter 48 (made up of a plurality of splitter segments 50A–50N). The fourth device layer 14 defines a plurality of sample injection channels 54A–54N. A first frit 52 is disposed between the mobile phase splitter 48 and the sample injection channels 54A–54N. The first frit 52 (and the other frits described below) is preferably constructed from a permeable polypropylene membrane such as, for example, 1-mil thickness Celgard 2500 membrane (55% porosity, 0.209×0.054 micron pore size, Celgard Inc., Charlotte, N.C.). The fifth and sixth device layers 15, 16 define a plurality of sample injection vias 56A–56N and 57A–57N. A second frit 58 is disposed between the sample injection vias 56A–56N in the fifth device layer 15 and the sample injection vias 57A–57N in the sixth device layer 16. The fifth through twelfth device layers 15–22 define the first mobile phase vias 64A–64H, which are in fluidic communication with each other and the mobile phase mixing channel 42.

The fifth and sixth device layers 15, 16 define second mobile phase mixer slits 60, 62, which are in fluidic communication with each other and the mobile phase mixing channel 42. The seventh device layer defines a channel segment 66, which is in fluidic communication with the second mobile phase mixer slits 60, 62 and a plurality of second mobile phase input vias 68A–68D and port 68E defined in the eighth through twelfth device layers 18–22.

The seventh device layer 17 defines the separation columns 29A–29N. The seventh device layer 17 together with the eighth device layer 18 define a slurry distribution network 70 that includes a slurry input channel 72 and a slurry splitter 74 (made up of slurry splitter segments 76A–76N). The eighth through twelfth device layers 18–22 define a plurality of slurry vias 78A–78N, which are in fluidic communication with each other and the slurry input channel 42.

The eight and ninth device layers 18, 19 define a plurality of separation column output vias 80A–80N in fluid communication with each other and the separation columns 29A–29N. A third frit 82 is interposed between the separation column output vias 80A–80N in the eight device layer 18 and the separation column output vias 80A–80N in the ninth device layer 19.

The tenth device layer 20 defines a plurality of output analysis channels 32A–32N, each including an optical alignment segment 86A–86N (which is aligned with the optical detection windows 30A–30N defined in the fourth through eight and twelfth device layers 14–18, 22. Effluent vias 89A–89N, 88A–88N are defined in the eleventh and twelfth device layers 21, 22 and are in fluid communication with each other and the output analysis channels 32A–32N. Fourth and fifth frits 90, 92 are interposed between the effluent vias 89A–89N in the eleventh device layer 21 and the effluent vias 88A–88N in the twelfth device layer 22.

In operation, the columns 29A–29N of the device 10 are packed with the desired stationary phase material, typically silica-based particulate such as C-18 silica particles. A slurry of a solvent (such as acetonitrile) and particulate is injected through the slurry vias 78A–78N into the slurry input channel 72 and the slurry splitter 74, whereupon the slurry is distributed to each of the columns 29A–29N. The second and third frits 58, 82 prevent the slurry from exiting the columns 29A–29N through either the separation column output vias 80A–80N or the sample injection vias 56A–56N. Once the columns 29A–29N are packed, the slurry input channel 72 may be sealed to prevent unpacking therethrough. Alternatively, solvent may be injected through the slurry input channel 72 during separations, allowing the fluidic pressure of the solvent to maintain the desired packing density.

To perform a chromatographic separation using the device 10, the packed device is placed in a chromatography instrument (described below). One or more solvents are provided to the device 10 through the first and second solvent input ports 64H, 68E. If two solvents are used (for example, to perform a gradient separation) the solvents are combined as the second solvent enters the solvent mixing channel 42 through the second mobile phase mixer slits 60, 62. The convoluted channel formed by channel segments 46A–46N serve to provide sufficient channel length to permit mixing downstream of the overlap between slit 62 and the mixing channel 42 (enhanced by the plurality of directional changes experienced by the mobile phase). After the mixing, the mobile phase enters the mobile phase splitter 48, where it is evenly distributed to each of the columns 29A–29N and flows out of the device through the effluent vias 89A–89N and outlet ports 88A–88N.

Once the device 10 is thoroughly wetted with mobile phase, the flow of mobile phase is suspended and samples are injected into the sample input ports 28A–28N. Once the samples are input, the sample input ports 28A–28N are sealed and the flow of mobile phase is resumed, carrying the samples through the columns 29A–29N thereby performing the desired separation. Analytical instruments (not shown) may observe the results of the separation through the optical detection windows 30A–30N. Alternatively, or additionally, the effluent may be collected from the effluent vias 88A–88N for additional analysis.

Preferably, the various layers 11–22 of the device 10 are fabricated from unoriented polypropylene and bonded using an adhesiveless thermal bonding method utilizing platens, as described above. This construction method yields chemically-resistant devices having high bond strength, both desirable attributes for withstanding a column packing process and subsequent operation to provide separation utility.

While the device 10 illustrated in FIGS. 2 and 3A–3E represents a preferred fluidic device, a wide variety of other fluidic devices may be used. In certain embodiments, fluidic device may include one or more tubes, particularly capillary tubes. For example, capillary tubes may be embedded in one or more channels of a microfluidic device.

In liquid chromatography applications, it is often desirable to alter the makeup of the mobile phase during a particular separation. If multiple separation columns are provided in a single integrated device (such as the device 10) and the makeup of the mobile phase is subject to change over time, then at a common linear distance from the mobile phase inlet it is desirable for mobile phase to have a substantially identical composition from one column to the next. This is achieved with the device 10 due to two factors: (1) volume of the path of each (split) mobile phase solvent substream is substantially the same to each column; and (2) each flow path downstream of the fluidic (mobile phase and sample) inlets is characterized by substantially the same impedance. The first factor, substantially equal substream flow paths, is promoted by design of the multi-splitters 48, 70. The second factor, substantial equality of the impedance of each column, is promoted by both design of the fluidic device 10 and the fabrication of multiple columns in fluid communication (e.g., having a common outlet) using the slurry packing method disclosed herein. Where multiple columns are in fluid communication with a common outlet, slurry flow within the device is biased toward any low impedance region. The more slurry that flows to a particular region during the packing process, the more particulate is deposited to locally elevate the impedance, thus yielding a self-correcting method for producing substantially equal impedance from one column to the next.

In another embodiment, illustrated in FIGS. 4 and 5A–5E, a device 400 includes twenty-four parallel separation channels 439A–439N containing stationary phase material. The device 400 may be constructed with twelve device layers 411–422, including multiple stencil layers 414–420 and two outer or cover layers 411, 422. Each of the twelve device layers 411–422 defines five alignment holes 423–427 (with hole 424 configured as a slot), which may be used in conjunction with external pins (not shown) to aid in aligning the layers during construction or in aligning the device 400 with an external interface (not shown) during a packing process or during operation of the device 400. Preferably, the device 400 is constructed with materials selected for their compatibility with chemicals typically utilized in performing high performance liquid chromatography, including, water, methanol, ethanol, isopropanol, acetonitrile, ethyl acetate, dimethyl sulfoxide, and mixtures thereof. Specifically, the device materials should be substantially non-absorptive of, and substantially non-degrading when placed into contact with, such chemicals. Suitable device materials include polyolefins such as polypropylene, polyethylene, and copolymers thereof, which have the further benefit of being substantially optically transmissive so as to aid in performing quality control routines (including checking for fabrication defects) and in ascertaining operational information about the device or its contents. For example, each device layer 411–422 may be fabricated from 7.5 mil (188 micron) thickness "Clear Tear Seal" polypropylene (American Profol, Cedar Rapids, Iowa).

Broadly, the device 400 includes various structures adapted to distribute particulate-based slurry material among multiple separation channels 439A–439N (to become separation columns upon addition of stationary phase material), to retain the stationary phase material within the device 400, to mix and distribute mobile phase solvents among the separation channels 439A–439N, to receive samples, to convey eluate streams from the device 400, and to convey a waste stream from the device 400.

The first through third layers 411–413 of the device 400 are identical and define multiple sample ports/vias 428A–428N that permit samples to be supplied to channels 454A–454N defined in the fourth layer 414. While three separate identical layers 411–413 are shown (to promote strength and increase the aggregate volume of the sample ports/vias 428A–428N to aid in sample loading), a single equivalent layer (not shown) having the same aggregate thickness could be substituted. The fourth through sixth layers 414–416 define a mobile phase distribution network 450 (including elements 450A–450N) adapted to split a supply of mobile phase solvent among twenty-four channel loading segments 454A–454N disposed just upstream of a like number of separation channels (columns) 439A–439N. Upstream of the mobile phase distribution network 450, the fourth through seventh layers 414–417 further define mobile phase channels 448–449 and structures for mixing mobile phase solvents, including a long mixing channel 442, wide slits 460A–460B, alternating channel segments 446A–446N (defined in the fourth and sixth layers 414–416) and vias 447A–447N (defined in the fifth layer 415).

Preferably, the separation channels 439A–439N are adapted to contain stationary phase material such as, for example, silica-based particulate material to which hydrophobic C-18 (or other carbon-based) functional groups have been added. One difficulty associated with prior microfluidic devices has been retaining small particulate matter within separation columns during operation. The present device 400 overcomes this difficulty by the inclusion of a downstream porous frit 496 and a sample loading porous frit 456. Each of the frits 456, 496 (and frits 436, 438) may be fabricated from strips of porous material, e.g., 1-mil thickness Celgard 2500 membrane (55% porosity, 0.209×0.054 micron pore size, Celgard Inc., Charlotte, N.C.) and inserted into the appropriate regions of the stacked device layers 411–422 before the layers 411–422 are laminated together. The average pore size of the frit material should be smaller than the average size of the stationary phase particles. Preferably, an adhesiveless bonding method such as one of the methods described previously herein is used to bond the device layers 411–422 (and frits 436, 438, 456, 496) together. Such methods are desirably used to promote high bond strength (e.g., to withstand operation at high internal pressures of preferably at least about 100 psi (690 kPa), more preferably at least about 500 psi (3450 kPa)) and to prevent undesirable interaction between any bonding agent and solvents and/or samples to be supplied to the device 400.

A convenient method for packing stationary phase material within the separation channels 439A–439N is to provide it to the device in the form of a slurry (i.e., particulate material mixed with a solvent such as acetonitrile). Slurry is supplied to the device 400 by way of a slurry inlet port 471 and channel structures defined in the seventh through ninth device layers 417–419. Specifically, the ninth layer 419 defines a slurry via 471A, a waste channel segment 472A, and a large forked channel 476A. The eighth device layer 418 defines two medium forked channels 476B and a slurry channel 472 in fluid communication with the large forked channel 476A defined in the ninth layer 419. The eighth layer 418 further defines eight smaller forked channels 476N each having three outlets, and twenty-four column outlet vias 480A–480N. The seventh layer 417 defines four small forked channels 476C in addition to the separation channels 439A–439N. In the aggregate, the large, medium, small, and smaller forked channels 476A–476N form a slurry distribution network that communicates slurry from a single inlet (e.g., slurry inlet port 471) to twenty-four separation channels 439A–439N (to become separation columns 439A–439N upon addition of stationary phase material). Upon addition of particulate-containing slurry to the separation channels 439A–439N, the particulate stationary phase material is retained within the separation channels by one downstream porous frit 496 and by one sample loading porous frit 456. After stationary phase material is packed into the columns 439A–439N, a sealant (preferably substantially inert such as UV-curable epoxy) is added to the slurry inlet port 471 to prevent the columns from unpacking during operation of the device 400. The addition of sealant should be controlled to prevent blockage of the waste channel segment 472A.

To prepare the device 400 for operation, one or more mobile phase solvents may be supplied to the device 400 through mobile phase inlet ports 464, 468 defined in the twelfth layer 422. These solvents may be optionally pre-mixed upstream of the device 400 using a conventional micromixer. Alternatively, these solvents are conveyed through several vias (464A–464F, 468A–468C) before mixing. One solvent is provided to the end of the long mixing channel 442, while the other solvent is provided to a short mixing segment 466 that overlaps the mixing channel 442 through wide slits 460A–460B defined in the fifth and sixth layers 415, 416, respectively. One solvent is layered atop the other across the entire width of the long mixing channel 442 to promote diffusive mixing. To ensure that the solvent mixing is complete, however, the combined solvents also flow through an additional mixer composed of alternating channel segments 446A–446N and vias 447A–447N. The net effect of these alternating segments 446A–446N and vias 447A–447N is to cause the combined solvent stream to contract and expand repeatedly, augmenting mixing between the two solvents. The mixed solvents are supplied through channel segments 448, 449 to the distribution network 450 including one large forked channel 450A each having two outlets, two medium forked channels 450B each having two outlets, four small forked channels 450C each having two outlets, and eight smaller forked channels 450N each having three outlets.

Each of the eight smaller forked channels 450A–450N is in fluid communication with three of twenty-four sample loading channels 454A–454N. Additionally, each sample loading channel 454A–454N is in fluid communication with a different sample loading port 428A–428N. Two porous frits 438, 456 are disposed at either end of the sample loading channels 454A–454N. While the first frit 438 technically does not retain any packing material within the device, it may be fabricated from the same material as the second frit 456, which does retain packing material within the columns 439A–439N by way of several vias 457A–457N. To prepare the device 400 for sample loading, solvent flow is temporarily interrupted, an external interface (not shown) previously covering the sample loading ports 428A–428N is opened, and samples are supplied through the sample ports 428A–428N into the sample loading channels 454A–454N. The first and second frits 438, 456 provide a substantial fluidic impedance that prevents fluid flow through the frits 438, 456 at low pressures. This ensures that the samples remain isolated within the sample loading channels 454A–454N during the sample loading procedure. Following sample loading, the sample loading ports 428A–428N are again sealed (e.g., with an external interface) and solvent flow is re-initiated to carry the samples onto the separation columns 439A–439N defined in the seventh layer 417.

While the bulk of the sample and solvent that is supplied to each column 439A–439N travels downstream through the columns 439A–439N, a small split portion of each travels upstream through the columns in the direction of the waste port 485. The split portions of sample and solvent from each column that travel upstream are consolidated into a single waste stream that flows through the slurry distribution network 476, through a portion of the slurry channel 472, then through the short waste segment 472A, vias 474C, 474B, a frit 436, a via 484A, a waste channel 485, vias 486A–486E, and through the waste port 486 to exit the device 400. The purpose of providing both an upstream and downstream path for each sample is to prevent undesirable cross–contamination from one separation run to the next, since this arrangement prevents a portion of a sample from residing in the sample loading channel during a first run and then commingling with another sample during a subsequent run.

Either isocratic separation (in which the mobile phase composition remains constant) or, more preferably, gradient separation (in which the mobile phase composition changes with time) may be performed. Following separation, the eluate may be analyzed by one or more detection techniques and/or collected for further analysis. Preferably, the eluate is analyzed using both flow-through optical-type detection (e.g., UV-Vis and/or fluorescence detection) and mass analysis such as mass spectrometry.

Preferred Systems

A system for performing high-throughput pressure-driven liquid chromatography is shown in FIG. 6. The system 700 preferably includes at least one (preferably at least two) solvent reservoir(s) 702 and pump(s) 704 for each solvent.

Reservoirs 702 and pumps 704 for two or more solvents may be provided to permit operation of the system 700 in gradient mode, in which the mobile phase solvent composition is varied with respect to time during a particular separation run. Preferred pumps include conventional high-pressure liquid chromatography (HPLC) pumps such as Alcott Model 765 HPLC pumps with microbore heads (Alcott Chromatography, Norcross, Ga.). A pulse damper 706 is preferably provided downstream of the pump(s) 704 to reduce variations in the mobile phase solvent supply pressure. A conventional micromixer (not shown) may be disposed between the pulse damper 706 and a multi-column microfluidic separation device 800 (such as devices 10, 100, 400 illustrated in and described in connection with FIGS. 1A, 2, 3A–3E, 4 and 5A–5E). A sample source 715 is also provided to provide samples to the microfluidic device 800 (preferably in parallel to permit parallel chromatographic separations of different samples). The interface with the microfluidic device 800 is provided by way of a seal plate 708A and a sample inlet seal 708B and one or more compression elements 710A, 710B that preferably include actuators (not shown). If desired, the seal plate 708A and sample inlet seal 708B may be moved individually by the compression elements 710A, 710B. The seal plate 708A and the sample inlet seal 708B may be used to provide intermittent sample access to the device 800, to conduct mobile phase solvent to the device 800, and to convey eluate from the device 800 following chromatographic separation.

Downstream of the separation device 800, and detector 718 preferably having multiple detection regions (not shown), one detection region corresponding to each separation column of the microfluidic device 800. While various detection technologies may be used, the detector 718 preferably includes an electromagnetic source and an electromagnetic receiver such as may be used for UV-Visible detection. It will be readily apparent to one skilled in the art that the detector 718 may be adapted to perform the desired detection on the eluate stream while it is still in the device 800 (as described above with respect to FIGS. 2 and 3A–3E) or in a flow cell downstream of the device 800 (as described above with respect to FIGS. 4 and 5A–5E). Downstream of the detector 718, eluate may be collected (e.g., for further analysis) or discarded in a collection or waste region 720.

Referring to FIGS. 7A–7F, in a preferred embodiment, a system 300 for performing multiple parallel liquid chromatography separations includes a plurality of stored microfluidic devices 302A–302N, a transport system 304, and a chromatography instrument 306. The microfluidic devices 302A–302N may be any suitable devices that include at least one separation column, or more preferably, multiple separation columns (such as the devices 10, 100, 400 described above). The transport system 304 may be any suitable automated system, such as a robot arm, which is capable of selecting one of the stored microfluidic devices 302 and moving it from a storage region 303 to the instrument 306. Alternatively, transport of the devices 302 may be performed manually by an operator (not shown).

The instrument 306 includes a mobile phase reservoir 308, a pressure source 310, a sample source 312, a device interface 314, one or more in-line analytical devices 316, one or more downstream analytical devices 318, a sample dump 320, and, optionally, a sample collector 322. The mobile phase reservoir 308 may include one or more containers (not shown) of liquids used as mobile phase material, such as water, acetonitrile, methanol or other suitable substances. By providing multiple containers, it is possible to perform separations using whichever material is most desirable for the particular analysis and/or performing gradient separations.

The sample source 312 may be any suitable supply of samples for analysis. For example, the sample source 312 may be a library of well plates, such as a 96-well microtiterplate, containing a variety of compounds of interest. Samples may be drawn directly from the sample source 312 into the device 302A through manual means, such as pipettors, a multi-pipettor or other suitable devices. Alternatively, an automated system for transferring samples into the device 302 may be provided, such as through automated multi-pipettors or microfluidic fluid management systems.

The pressure source 310 may be any suitable pump, including high-pressure pumps, such as the Shimadzu LC-10AT (Shimadzu Scientific Instruments, Inc., Columbia, Md.). Multiple pumps 310 may be provided to permit the use of multiple mobile phases, such as may be desirable for performing gradient separations or to allow the performance of various separation protocols on a single device 306. In a preferred embodiment, the pressure source 310 is capable of executing a linear, binary gradient in 0.1-minute increments. In addition, the pressure source provides pressures up to about five hundred psi. (about 35.15 $kg/cm^2$), a flow rate of about 10–200 mL/min adjustable in 1 mL increments, pulsation less than about 1%, and accuracy of about±1%.

The device interface 314 may include components such as described above for providing mobile phase and or samples to the microfluidic device 302. Referring to FIGS. 4D–4F, device interface 314 includes a frame 900; a manifold 801 that includes a first plate or device base-plate 802, a second plate or device top-plate 804 (a moveable plate), an inlet/outlet conduit ("I/O conduit") 806, and a sample inlet seal 810; a top-plate actuator 808 (the first compression element), a sample inlet seal actuator 812 (the second compression element), and actuator controls 814.

The frame 900 is preferably fabricated with aluminum, steel, polymer, or any other suitable material that provides the desired rigidity and stability. The base-plate 802 is adapted to receive a microfluidic device 302A, with a slot 816 or, alternatively, registration pins (not shown) or other device alignment structures, for positioning the microfluidic device 302A appropriately within the device interface 314. The device top-plate 804 also may include a slot 818 for receiving the microfluidic device 302A or may include other positioning means (not shown) as may be appropriate. The I/O conduit 806 is positioned within the base plate 802 so that it corresponds to the fluid inlets and outlets of the device 302A when the microfluidic device 302A is positioned within the interface 314. The I/O conduit 806 may include an interface (not visible) such as the interface 200 described above (adapted to provide the desired number of inlets and outlets). The top-plate 804 is adapted to be moved up and down by the top-plate actuator 808 so that the microfluidic device 320A may be secured within the interface 314. When the top-plate 804 is in the down position, pressure is exerted against the microfluidic device 302A, pressing the device 302A against the base-plate 802 and the I/O conduit 806, thereby forming a substantially fluid tight seal such as that described above with respect to interface 200. The I/O inlet 806 may be used to provide mobile phase to the device 302A through mobile phase inlets (such as the solvent inlets 64H, 68H described above with respect to the device 10).

It will be readily apparent to one skilled in the art that any fluidic inlets or outlets may be positioned as desired on any surface of the microfluidic device 320A. Accordingly, any inlets or outlets of the interface 314 may be located on the base-plate 802, top-plate 804 or inlet seal 810, as appropriate. Also, the microfluidic device 320A is preferably a planar device. Accordingly, the base-plate 802 and top-plate 804 are preferably substantially planar in order to provide uniform contact between the plates and the microfluidic device 320A and the desired fluidic sealing and compression of the device. Of course, the microfluidic device 320A could be curved or otherwise non-planar with correspondingly non-planar base-plates 802 and top-plates 804, provided the desired seals and compression are maintained.

The sample inlet seal 810 is adapted to move both vertically and laterally (i.e., with two degrees of freedom) with respect to the top-plate 804 and the microfluidic device 302A. In the closed position, the sample inlet seal 810 is pressed against the microfluidic device 302A (through an opening in the top-plate 804), sealing the sample inlets (e.g., inlets 113A–113N, 28A–28N, or 428A–428N such as shown in FIGS. 1A, 1B, 2, 3A–3E, 4 and 5A–5E) thereby preventing leakage, pressure loss and/or sample loss during operation. Notably, the sample inlet seal 810 and top-plate 804 are mounted on guide rails 850A–850N. The guide rails 850A–850N ensure that the top-plate 804 and sample inlet seal 810 may be moved in a linear fashion, providing even compression against the microfluidic device 302A to create adequate seals. During sample loading, the sample inlet seal 810 may be moved up and aside to allow access to the sample inlets (e.g., inlets 113A–113N, 28A–28N) of the microfluidic device 302A. The actuators 808, 812 may be controlled manually using the actuator controls 814 or may be controlled remotely by an operator (not shown) or a control system (not shown). The top-plate 804 and base-plate 802 may include windows 820, 822 to allow analytical devices to be connected to the interface 314 to allow observation or analysis of portions of the microfluidic device 302A. It will be readily apparent to one skilled in the art that the geometry of the components may be varied as desired. For example, the top-plate 804 and sample inlet seal 810 may be positioned on opposite sides of the base-plate 802.

Figure 7E:
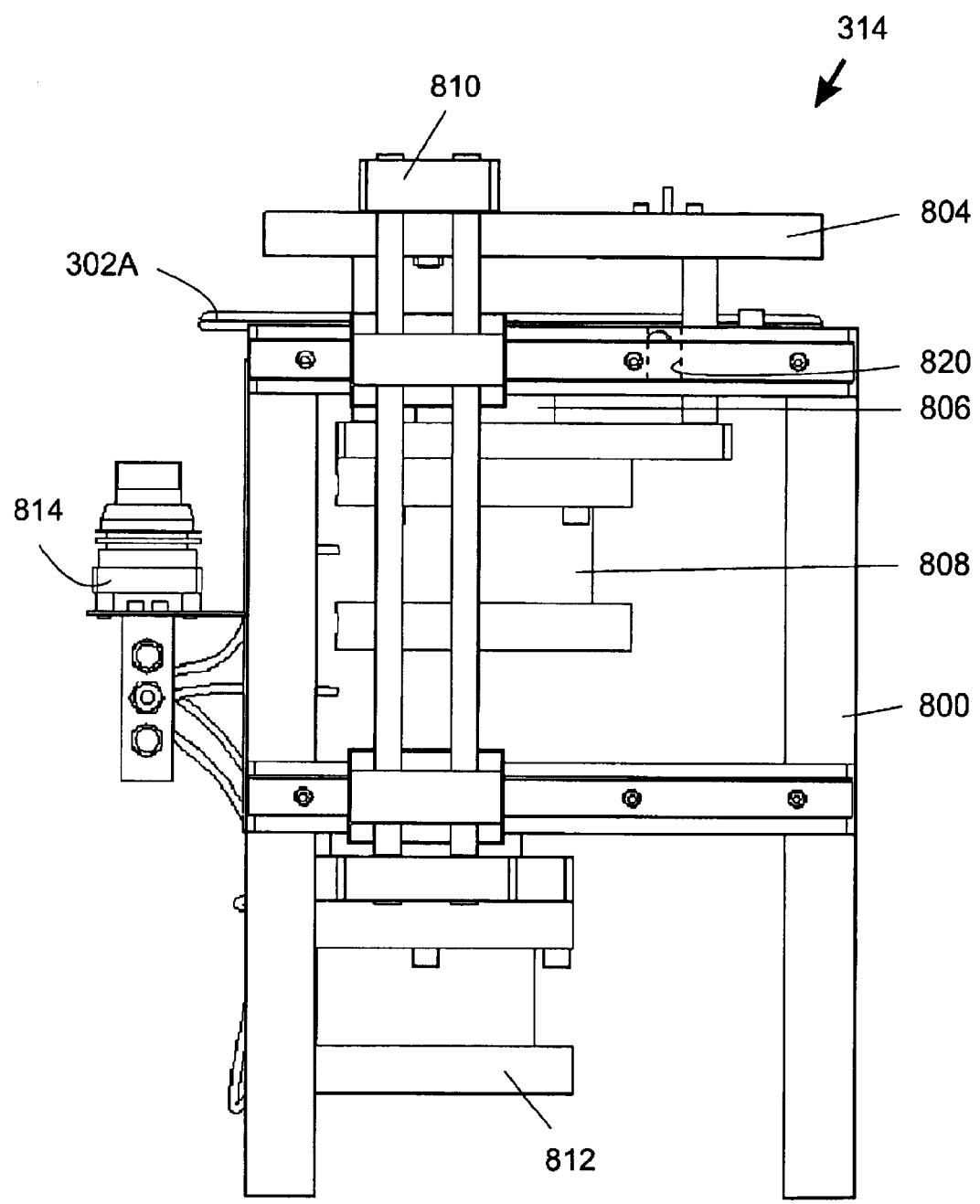
FIG. 7E is a side view of the device interface portion of the system of FIG. 7A.
Figure 7F:
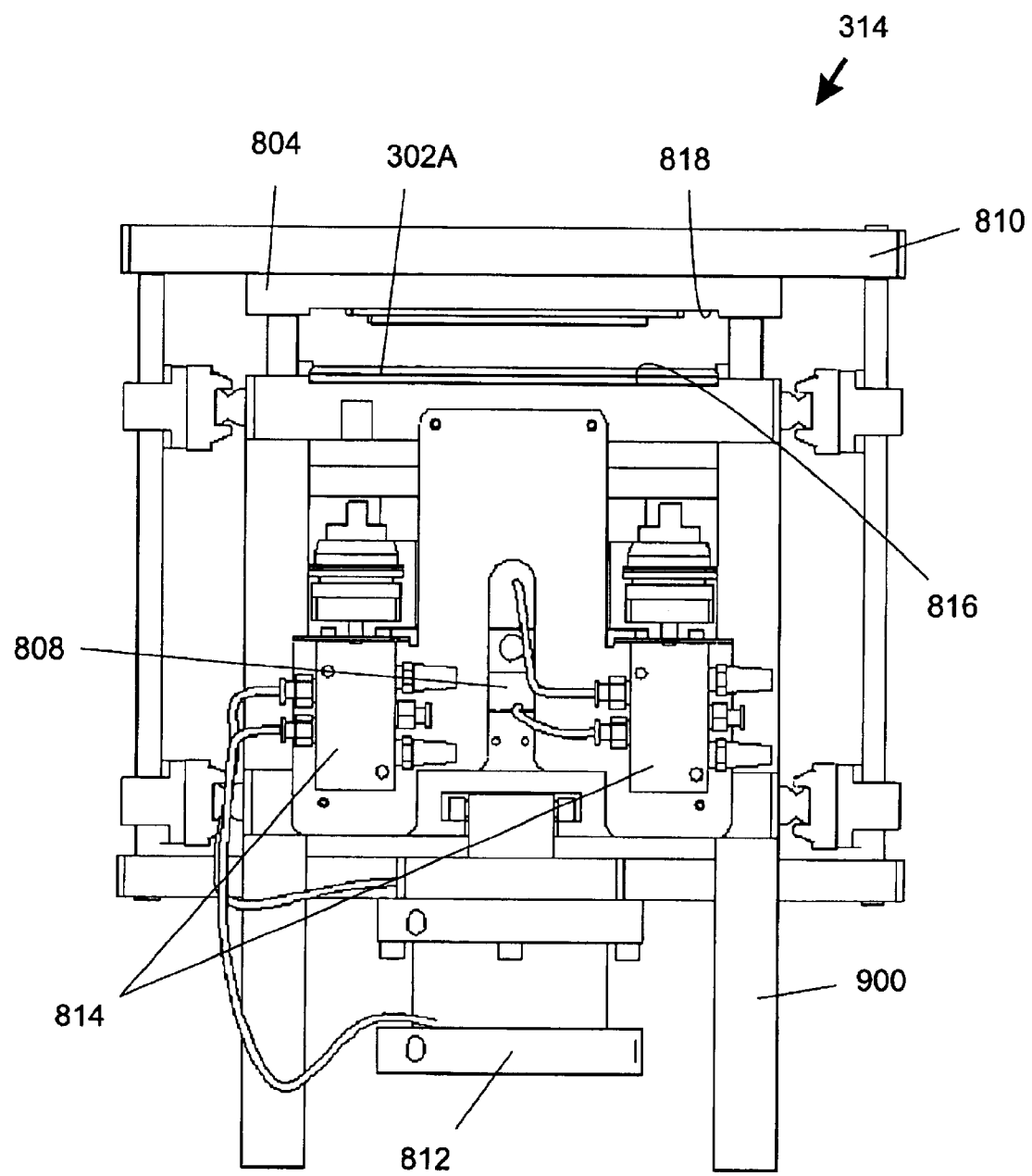
FIG. 7F is a front view of the device interface portion of the system of FIG. 7A.

The particular configuration of the interface illustrated in FIGS. 7D–7F is adapted to function with the twenty-four column microfluidic device 302A described above with reference to FIGS. 2A–2B. It will be readily appreciated by one skilled in the art that that the presence and/or position of any of the elements of the interface 314 may be altered to adapt to microfluidic devices with different numbers of columns or inlets, outlets, analysis windows, or other features and structures positioned differently than in that device. Likewise, the instrument 306 may be altered to accommodate alternative devices, including more or less columns, samples, analytical devices, or other modifications that would be desirable and apparent to one skilled in the art. For example, the instrument may be adapted to include a flow cell downstream of a microfluidic device such as that shown in FIGS. 4 and 5A–5E so that optical detection may be performed off-board of the microfluidic device.

The analytical devices 316, 318 may be any devices for performing desirable analyses of the output from the microfluidic devices 302 and may include, without limitation, devices for performing UV-visible spectroscopy, Raman spectroscopy, fluorescence detection, chemiluminescence, electrochemical detection, other electronic detections such as capacitive and conductivity measurement, mass spectrometry, nuclear magnetic resonance, evaporative light scattering, ion mobility spectrometry, and/or matrix-assisted laser desorption ionization (MALDI).

In a preferred embodiment, the in-line analytical device 316 comprises a UV spectroscope having a lamp 901, illumination optical fibers 902, receiver optical fibers 904, sensor 906, and A/D converter 908. Preferably, the spectroscope 316 has a deuterium UV source; focusing, collimation and alignment optics made from a combination of lenses and fibers; UV filters at selectable wavelengths: 214 nm, 254 nm, 280 nm; bandpass filters at about 10 nm FWHM; a detection wavelength range of about 214–280 nm; an absorbance dynamic range of about 5.0'10-4-1.0 absorbance units (A.U.); RMS noise of less than about 5.0'10-4 A.U. for one second integration; and drift of about 5.0'10-4 A.U.

The in-line analytical device 316 also includes a twenty-four bit analog to digital converter (no missing code; minimum nineteen bits effective resolution); a dynamic range of up to about one-hundred dB, bandwidth of up to about one-hundred Hz alias-free bandwidth per detection channel; and 1 kS/s maximum sampling rate. The analytical device 316 preferably includes the capability to simultaneously sample twenty-four analog input channels per detection printed wire board (PWB), with each channel having programmable gain.

In a preferred embodiment, the off-line analytical device 318 comprises a mass spectrometer. The output of the microfluidic device 302A may be routed to a multiplexing system or may be stored in storage or delay lines to allow continuous analysis of the output (e.g., see commonly-assigned co-pending U.S. application Ser. No. 10/637,234, filed Aug. 8, 2003).

The sample dump 320 may be any suitable container for disposal of the unused fluid stream exiting the microfluidic device 302.

The sample collection device 322 may be any suitable container for collecting one or more portions of the fluid stream for later use, such as a fraction collector (see commonly-assigned co-pending U.S. patent application Ser. No. 10/147,948, filed May 16, 2002).

In operation, the following steps are performed using the system 300:

1. A microfluidic device is selected;
2. The microfluidic device is loaded into the instrument;
3. The manifold secures microfluidic device solvent and inlet ports;
4. The instrument injects solvent(s) to pre-wet and condition the columns for a suitable period of time;
5. The instrument depressurizes the microfluidic device;
6. The sample inlet seal is released to expose the sample inlets;
7. Samples are loaded into the inlet ports of the microfluidic device;
8. The sample inlet seal is secured;
9. The instrument injects samples onto column(s);
10. The instrument delivers mobile phase to the microfluidic device, performs the separations and UV detection;
11. The instrument generates a chromatogram that may be displayed on a computer monitor and/or archived in a data file;
12. The manifold is released and the microfluidic device is removed; and
13. The instrument undergoes a wash cycle to prepare for the next microfluidic device.

The output from the separations may then be analyzed by the analytical devices 316, 318. Some or all of the output may be collected for further study in the sample collector 322. Any remaining output may be discarded in the sample dump 320.

Systems for performing multiple parallel liquid chromatographic separations according to the present invention provide a number of advantages. For example, the use of microfluidic chips that contain multiple separation columns allow multiple separations to be performed in a limited space. Also, the use of pressure fit interfaces such as those described above allow such microfluidic chips to easily be removed and replaced within a chromatography instrument, either manually or robotically.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. A system for performing parallel liquid chromatography comprising:
   a microfluidic device defining a plurality of chromatographic separation columns, a plurality of sample inlet ports, a mobile phase inlet port, and an eluate port;
   a frame;
   a first plate affixed to the frame;
   a second plate movably affixed to the frame; and
   a sample inlet seal movably affixed to the frame, wherein the sample inlet seal may be moved independently of the second plate;
   wherein the first plate and second plate are adapted to compressively secure the microfluidic device;
   wherein the sample inlet seal is adapted to seal the plurality of sample inlet ports; and
   wherein any of the first plate and the second plate are adapted to engage at least one of the mobile phase inlet port and the eluate port.

2. The system of claim 1 further comprising a first compression element affixed to the frame and the top seal plate.

3. The system of claim 2 further comprising a second compression element affixed to the frame and the sample inlet seal plate.

4. The system of claim 1 wherein:
   the first plate defines a first surface and a second surface;
   the second plate is disposed adjacent to the first surface; and
   the sample inlet seal is disposed adjacent to the second surface.

5. The system of claim 1 wherein the first plate defines a first surface and a second surface and the second plate and the sample inlet seal are disposed adjacent to the first surface.

6. The system of claim 1 further comprising a guide rail affixed to the frame and the second plate.

7. The system of claim 1 further comprising a guide rail affixed to the frame and the sample inlet seal.

8. The systems of claim 1 wherein the sample inlet seal is capable of movement with at least two degrees of freedom.

9. The system of claim 1 wherein the microfluidic device further comprises a plurality of eluate ports.

10. The system of claim 1 wherein the microfluidic device further comprises a plurality of mobile phase inlet ports 11. The system of claim 1 wherein the microfluidic device is substantially planar.

12. The system of claim 1 wherein the microfluidic device comprises a plurality of device layers.

13. The system of claim 12 wherein at least one of the device layers is a stencil layer.

14. The system of claim 12 wherein any device layer of the plurality of device layers is a polymer layer.

15. The system of claim 14 wherein each device layer of the plurality of device layers is an adhesiveless polymer layer.

16. The system of claim 14 wherein the polymer layer is a vinyl-based polymer.

17. The system of claim 14 wherein the polymer layer is a polyolefin.

18. The system of claim 14 wherein the polymer layer is polypropylene.

* * * * *